US009629870B2

(12) United States Patent
Putnam et al.

(10) Patent No.: US 9,629,870 B2
(45) Date of Patent: Apr. 25, 2017

(54) POLYMER COMPOSITIONS OF DIHYDROXYACETONE AND USES THEREOF

(71) Applicant: Cornell University, Ithaca, NY (US)

(72) Inventors: David Putnam, Ithaca, NY (US); Peter Zaweneh, Cambridge, MA (US); Jason Spector, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 14/548,899

(22) Filed: Nov. 20, 2014

(65) Prior Publication Data

US 2015/0079019 A1    Mar. 19, 2015

Related U.S. Application Data

(66) Division of application No. 13/127,464, filed as application No. PCT/US2009/063177 on Nov. 3, 2009, now Pat. No. 8,916,143, Substitute for application No. 61/110,734, filed on Nov. 3, 2008.

(51) Int. Cl.
*A61K 31/765* (2006.01)
*C08G 64/42* (2006.01)
*A61L 26/00* (2006.01)

(52) U.S. Cl.
CPC .......... *A61K 31/765* (2013.01); *A61L 26/008* (2013.01); *A61L 26/0019* (2013.01); *C08G 64/42* (2013.01)

(58) Field of Classification Search
CPC .............................. A61L 26/0019; C08L 61/02
See application file for complete search history.

(56) References Cited

U.S. PATENT DOCUMENTS

| | | | |
|---|---|---|---|
| 4,049,795 | A | 9/1977 | Laborit |
| 6,231,837 | B1 | 5/2001 | Stroud et al. |
| 7,910,135 | B2 | 3/2011 | St. John et al. |
| 8,916,143 | B2 | 12/2014 | Putnam et al. |
| 2008/0194786 | A1 | 8/2008 | Putnam et al. |
| 2010/0104623 | A1 | 4/2010 | Harashima et al. |

OTHER PUBLICATIONS

CRC Polymers for Controlled Drug Delivery, Peter J. Tarcha, 191, p. 16.*
Abe, M. et al., A randomized controlled trial on the prevention of seroma after partial or total mastectomy and axillary lymph node dissection, Breast Cancer, 5(1):67-69 (1998).
Agrawal, A. et al., Concepts of seroma formation and prevention in breast cancer surgery, ANZ Journal of Surgery, 76:1088-1095 (2006).
Aitken, D.R. et al., Prevention of seromas following mastectomy and axillary dissection, Surgery, Gynecology and Obstetrics, 158:327-330 (1984).
Alvandi, R.Y. et al., Preliminary results of conservative treatment of early breast cancer with axillary dissection and post operative radiotherapy. A retrospective review of 107 patients, The Australian and New Zealand Journal of Surgery, 61(9):670-674 (1991).
Barbucci, R. et al.,Synthesis, chemical and rheological characterization of new hyaluronic acid-based hydrogels, Journal of Biomaterials Science-Polymer Edition, 11(4):383-399 (2000).
Barbucci, R. Hydrogels, Biological Properties and Applications, 53-54 (2009).
Budd, D.C. et al., Surgical morbidity after mastectomy operations, The American Journal of Surgery, 135:218-220 (1978).
Carless, P.A. and Henry, D.A., Systematic review and meta-analysis of the use of fibrin sealant to prevent seroma formation after breast cancer surgery, British Journal of Surgery, 93:810-819 (2006).
Chilson, T.R. et al., Seroma prevention after modified radical-mastectomy, The American Surgeon, 58:750-754 (1992).
Coveney, E.C. et al., Effect of closing dead space on seroma formation after mastectomy—a prospective randomized clinical trial, European Journal of Surgical Oncology, 19:143-146 (1993).
Davis, L., Structure of dihydroxyacetone in solution, Bioorganic Chemistry, 2:197-201 (1973).
Ferroni, E.L. et al., A three-step preparation of dihydroxyacetone phosphate dimethyl acetal, Journal of Organic Chemistry, 64:4943-4945 (1999).
Gilbert, T. et al., Lysine-derived urethane surgical adhesive prevents seroma formation in a canine abdominoplasty model, Plastic and Reconstructive Surgery 122:95-102 (2008).
Gilding, D.K. and Reed, A.M., Biodegradable polymers for use in surgery—poly(ethylene oxide)/poly(ethylene terephthalate) (PEO/PET) copolymers: 2. In vitro degradation, Polymer, 22(4):499-504 (1981).
Gilding, D.K. and Reed, A.M., Biodegradable polymers for use in surgery-poly(ethylene oxide) poly(ethylene terephthalate) (PEO/PET) copolymers: 1, Polymer, 20(12):1454-1458 (1979).
Harada, R.N. et al., Fibrin glue reduces seroma formation in the rat after mastectomy, Surgery, Gynecology and Obstetrics, 175:450-454 (1992).
Hayes, J.A. and Bryan, R.M., Wound-healing following mastectomy, The Australian and New Zealand Journal of Surgery, 54:25-27 (1984).
He, X.W. et al., Physical gelation of a multiblock copolymer—Effect of copolymer composition, Macromolecules, 21:1757-1763 (1988).
He, X.W. et al., Physical gelation of a multiblock copolymer—Effect of solvent type, Macromolecules, 22:1390-1397 (1989).
Henderson, P.W., et al. A rapidly resorbable hemostatic biomaterial based on dihydroxyacetone, Journal of Biomedical Materials Research Part A, 93(2):776-782 (2009).
Hubbell, J.A. Synthetic biodegradable polymers for tissue engineering and drug delivery, Current Opinion in Solid State and Materials Science, 3:246-251 (1998).

(Continued)

*Primary Examiner* — Alma Pipic
(74) *Attorney, Agent, or Firm* — Choate, Hall and Stewart LLP; John P. Rearick; Su Kyung Suh

(57) ABSTRACT

The present disclosure provides injectable synthetic and biodegradable polymeric biomaterials that effectively prevent seroma, a common postoperative complication following ablative and reconstructive surgeries. Provided biomaterials include physically crosslinked hydrogels that are thixotropic, display rapid chain relaxation, are easily extruded through narrow gauge needles, biodegrade into inert products, are well tolerated by soft tissues, and effectively prevent seroma in a radical breast mastectomy animal model.

21 Claims, 13 Drawing Sheets

(56) References Cited

OTHER PUBLICATIONS

International Search Report for PCT/US2009/063177 mailed Jun. 1, 2010.
Kato, N. et al., Dihydroxyacetone production from methanol by a dihydroxyacetone kinase deficient mutant of hansenula-polymorpha, Applied Microbiology and Biotechnology, 23:180-186 (1986).
Kuroi, K. et al., Pathophysiology of seroma in breast cancer, Breast Cancer 12(4):288-293 (2005).
Langer, R., and Tirrell, D.A., Designing materials for biology and medicine, Nature, 428:487-492 (2004).
Lindsey, W.H. et al., Seroma prevention using fibrin glue in a rat mastectomy model, Archives of Surgery, 125:305-307 (1990).
Nguyen, B.C. and Kochevar, I.E., Influence of hydration on dihydroxyacetone-induced pigmentation of stratum corneum, The Journal of Investigative Dermatology, 120:655-661 (2003).
Nowak, A.P. et al., Rapidly recovering hydrogel scaffolds from self-assembling diblock copolypeptide amphiphiles, Nature, 417:424-428 (2002).
Nyrkova, I.A. et al., Microdomains in Block-Copolymers and Multiplets in Ionomers—Parallels in Behavior, Macromolecules, 26:3601-3610 (1993).
O'Dwyer, P.J. et al., Effect of closing dead space on incidence of seroma after mastectomy, Surgery, Gynecology and Obstetrics, 172:55-56 (1991).
O'Hea, B.J. et al., External compression dressing versus standard dressing after axillary lymphadenectomy, American Journal of Surgery, 177:450-453 (1999).
Osteen, R.T. and Karnell, L.H., The national cancer data-base report on breast-cancer, Cancer, 73(7):1994-2000 (1994).
Putnam, D., Polymers for gene delivery across length scales, Nature Materials, 5:439-451 (2006).
Rice, D.C. et al., Intraoperative topical tetracycline sclerotherapy following mastectomy: A prospective, randomized trial, Journal of Surgical Oncology, 73:224-227 (2000).
Roses, D. F. et al., Complications of level I and II axillary dissection in the treatment of carcinoma of the breast, Annals of Surgery, 230(2):194-201 (1999).
Sahiner, N. et al., Rheological characterization of a charged cationic hydrogel network across the gelation boundary, Polymer, 47, 1124-1131 (2006).
Sanders, R.P. et al., Effect of fibrinogen and thrombin concentrations on mastectomy seroma prevention, Journal of Surgical Research, 61:65-70 (1996).
Say, C.C. and Donegan, W., Biostatistical evaluation of complications from mastectomy, Surgery, Gynecology and Obstetrics, 138:370-376 (1974).
Schwabegger, A. et al., Seroma as a common donor site morbidity after harvesting the latissimus dorsi flap: Observations on cause and prevention, Annals of Plastic Surgery, 38(6):594-597 (1997).
Silverman, R.P. et al., Transdermal photopolymerized adhesive for seroma prevention, Plastic and Reconstructive Surgery, 103:531-535 (1999).
Singh et al., Poly-dihydroacetate: A novel biodegradable bioadhesive for use in reconstructive surgery, Journal of the American College of Surgeons, 207(3):S64 (2008).
Soler, C. and Soley, M., Rapid and delayed-effects of epidermal growth-factor on gluconeogenesis, Biochemical Journal, 294:865-872 (1993).
Supplementary European Search Report for EP09829696.5, 5 pages (Mar. 1, 2013).
Tangpasuthadol, V. et al., Hydrolytic degradation of tyrosine-derived polycarbonates, a class of new biomaterials. Part I: Study of model compounds, Biomaterials, 21:2371-2378 (2000).
Tekin, E. et al., Seroma prevention by using Corynebacterium parvum in a rat mastectomy model, European Surgical Research, 33:245-248 (2001).
Terrell, G.S. and Singer, J.A., Axillary versus combined axillary and pectoral drainage after modified radical-mastectomy, Surgery, Gynecology and Obstetrics, 175:437-440 (1992).
Vermonden, T. et al., Rheological studies of thermosensitive triblock copolymer hydrogels, Langmuir, 22:10180-10184 (2006).
Wang, J.Y. et al., Seroma prevention in a rat mastectomy model: Use of a light-activated fibrin sealant, Annals of Plastic Surgery, 37:400-405 (1996).
Wang, L.W. et al., Structure formation in injectable poly(lactide-co-glycolide) depots. II. Nature of the gel, Journal of Biomedical Materials Research, 72B:215-222 (2005).
Wong, S.Y. et al., Polymer systems for gene delivery-past, present, and future, Progress in Polymer Science, 32:799-837 (2007).
Woodworth, P.A. et al., Seroma formation after breast cancer surgery: Incidence and predicting factors, The American Surgeon, 66(5):444-450 (2000).
Zawaneh et al., Diblock Copolymers Based on Dihydroxyacetone and Ethylene Glycol: Synthesis, Characterization, and Nanoparticle Formulation, Biomacromolecules 7: 3245-3251 (2006).
Zelikin et al., A Functionalizable Biomaterial Based on Dihydroxyacetone, and Intermediate of Glucose Metabolism, Biomacromolecules 7:3239-3244 (2006).
Zhu, K.J. et al., Synthesis, properties, and biodegradation of poly(1,3-Trimethylene Carbonate), Macromolecules, 24:1736-1740 (1991).

* cited by examiner

POLYMER COMPOSITIONS OF DIHYDROXYACETONE AND USES THEREOF

CROSS REFERENCE TO RELATED APPLICATIONS

The present application is a divisional of U.S. patent application Ser. No. 13/127,464, filed May 3, 2011, which claims priority under 35 U.S.C. §119(e) to U.S. provisional application U.S. Ser. No. 61/110,734, filed Nov. 3, 2008, the entire contents of which are hereby incorporated by reference.

GOVERNMENT SUPPORT

This invention was made with United States Government support under grant CBET-0642509 awarded by the National Science Foundation. The United States Government has certain rights in the invention.

BACKGROUND OF THE INVENTION

Seromas are a postoperative accumulations of serous fluid and are one of the most common complications in surgery today. Conventional wound management techniques are commonly applied when a seroma becomes a clinical concern. Placement of a seroma catheter or additional drain, as well as repeated or serial drainage of a seroma, may be required. Such complications result in a significant amount of lost income to patients, as well as expenses to insurers and physicians who have to care for these patients that require serial drainage. Such complications also delay wound healing, may entail additional surgical procedures, and ultimately delay the patient's return to work and routine functional activity. Seroma management can also be costly and, further, can place health care workers to additional needle exposure risks and related outcomes.

Several approaches to reduce seroma formation have been investigated. Surgical techniques, such as collapsing the seroma cavity with sutures, do not consistently and adequately eliminate seroma formation (Chilson, supra; Odwyer, P. J., O'Higgins, N. J., James, A. G. (1991); "Effect of closing dead space on incidence of seroma after mastectomy." *Surg Gynecol Obstet* 172, 55-56; Covency, E. C., O'Dwyer, P. J., Geraghty, J. G., O'Higgins, N.J. (1993) "Effect of closing dead space on seroma formation after mastectomy—a prospective randomized clinical trial." *Eur J Sur Oncol* 19, 143-146). Other methods, such as sclerotherapy (Tekin, E., Kocdor, M. A., Saydam, S., Bora, S., Harmancioglu, O. (2001) "Seroma prevention by using *Corynebacterium parvum* in a rat mastectomy model." *Eur Surg Res* 33, 245-248; Rice, D. C., et al. (2000) "Intraoperative topical tetracycline sclerotherapy following mastectomy: A prospective, randomized trial." *J Surg Oncol* 73, 224-227), compression dressings (O'hea, B. J., Ho, M. N., Petrek, J. A. (1999) "External compression dressing versus standard dressing after axillary lymphadenectomy." *Am J Surg* 177, 450-453), and biological adhesives, particularly fibrin glue (Lindsey, W. H., Masterson, T. M., Spotnitz, W. D., Wilhelm, M. C., Morgan, R. F. (1990) "Seroma prevention using fibrin glue in a rat mastectomy model." *Arch Surg* 125, 305-307; Harada, R. N., Pressler, V. M., McNamara, J. J. (1992) "Fibrin glue reduces seroma formation in the rat after mastectomy." *Surg Gynecol Obstet* 175, 450-454; Wang, J. Y., et al. (1996) "Seroma prevention in a rat mastectomy model: Use of a light-activated fibrin sealant." *Ann Plast Surg* 37, 400-405; Sanders, R. P., et al. (1996) "Effect of fibrinogen and thrombin concentrations on mastectomy seroma prevention." *J Surg Res* 61, 65-70; Carless, P. A., Henry, D. A. (2006) "Systematic review and meta-analysis of the use of fibrin sealant to prevent seroma formation after breast cancer surgery." *Brit J Surg* 93, 810-819), have not significantly decreased the clinical incidence of seroma formation. The current lack of effective methods available to medical practitioners dealing with seromas highlights the need for new methods for the prevention or treatment of seromas.

SUMMARY OF THE INVENTION

The present disclosure provides compositions of polydihydroxyacetone (pDHA) and methods of using the same. In some embodiments, provided compositions are copolymers of pDHA. In certain embodiments, provided copolymers are useful for treating and/or preventing seromas. In certain embodiments, provided copolymers are useful for treating and/or preventing post-operative tissue adhesion. In some embodiments, provided copolymers are useful for achieving hemostasis.

DEFINITIONS

Figure 1:
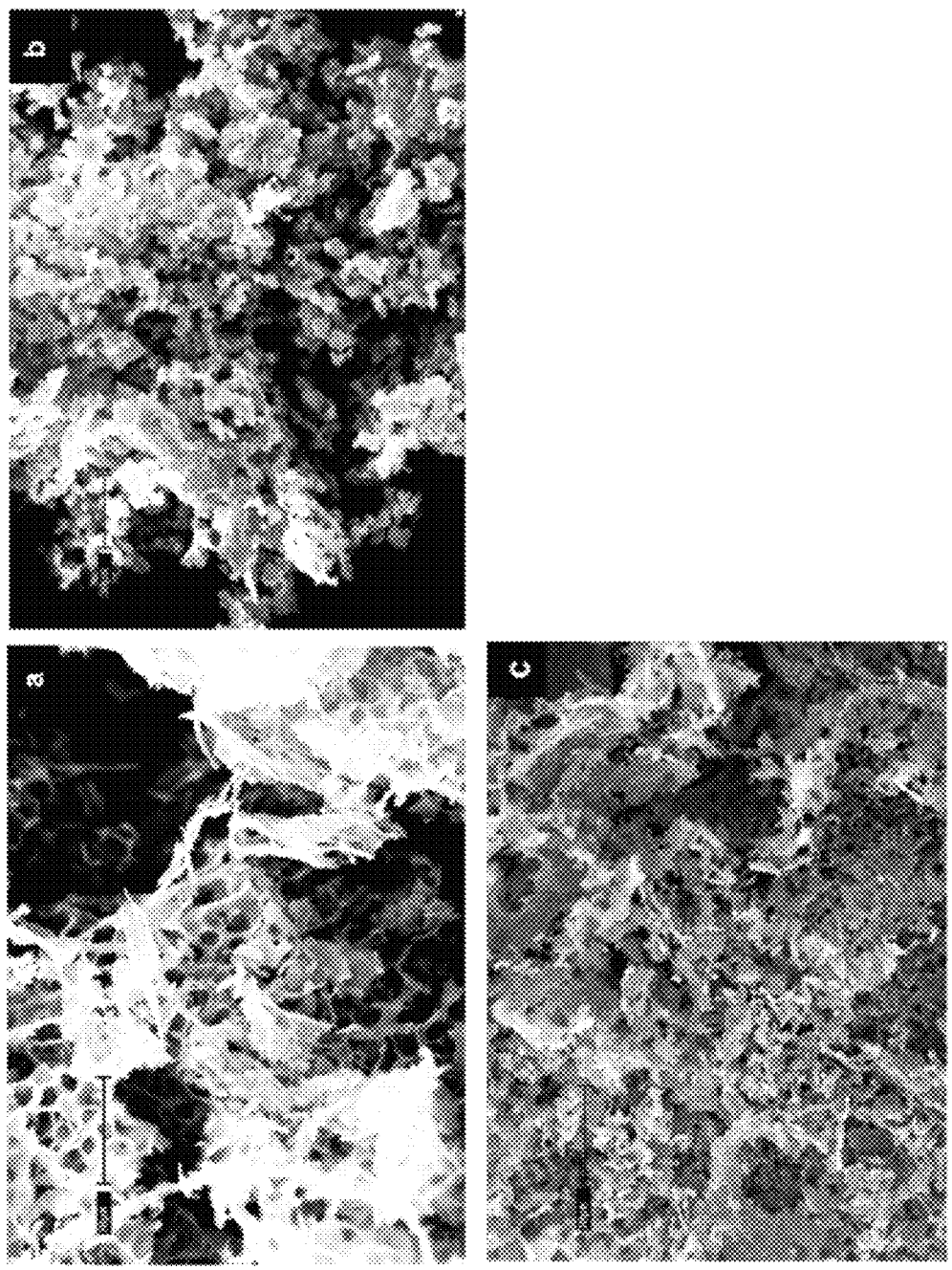
FIG. 1 depicts scanning electron micrographs (SEMs) of lyophilized MPEG-pDHA gels. (a) 5000-3000, (b) 5000-5000, (c) 5000-7000. Increasing the pDHA chain length reduces the hydrogel porosity.

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in *Organic Chemistry*, Thomas Sorrell, University Science Books, Sausalito: 1999, and *March's Advanced Organic Chemistry*, 5$^{th}$ Ed., Ed.: Smith, M. B. and March, J., John Wiley & Sons, New York: 2001, the entire contents of which are hereby incorporated by reference.

The term "acyl," used alone or a part of a larger moiety, refers to groups formed by removing a hydroxy group from a carboxylic acid. Such acyl groups include —C(=O) aliphatic, —C(=O)aryl, —C(=O)heteroaliphatic, or —C(=O)heteroaryl groups. Exemplary acyl groups include, without limitation, —C(=O)Me, —C(=O)Et, —C(=O)i-Pr, and —C(=O)CH$_2$F.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic, that has a single point of attachment to the rest of the molecule. Unless otherwise specified, aliphatic groups contain 1-6 aliphatic carbon atoms. In some embodiments, aliphatic groups contain 1-5 aliphatic carbon atoms. In some embodiments, aliphatic groups contain 1-4 aliphatic carbon atoms. In some embodiments, aliphatic groups contain 1-3 aliphatic carbon atoms, and in some embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic," as used herein, refers to aliphatic groups wherein one or more carbon atoms are independently replaced by one or more atoms selected from the group consisting of oxygen, sulfur, nitrogen, phosphorus, or silicon. In certain embodiments, one to six carbon atoms are independently replaced by one or more of oxygen, sulfur, nitrogen, or phosphorus. Heteroaliphatic groups may be substituted or unsubstituted, branched or unbranched, cyclic or acyclic, and include saturated, unsaturated or partially unsaturated groups.

The term "unsaturated," as used herein, means that a moiety has one or more units of unsaturation.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH═CHPh, which may be substituted with R°; —NO$_2$; —CN; —N$_3$—(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)N(R°)$_2$; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°)$_2$; or —(C$_{1-4}$ straight or branched) alkylene)C(O)O—N(R°)$_2$, wherein each R° may be substituted as defined below and is independently hydrogen, C$_{1-8}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3- to 12-membered saturated, partially unsaturated, or aryl mono- or polycyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^•$, -(haloR$^•$), —(CH$_2$)$_{0-2}$OH, —(CH$_2$)$_{0-2}$OR$^•$, —(CH$_2$)$_{0-2}$CH(OR$^•$)$_2$; —O(haloR$^•$), —CN, —N$_3$, —(CH$_2$)$_{0-2}$C(O)R$^•$, —(CH$_2$)$_{0-2}$C(O)OH, —(CH$_2$)$_{0-2}$C(O)OR$^•$, —(CH$_2$)$_{0-4}$C(O)N(R°)$_2$; —(CH$_2$)$_{0-2}$SR$^•$, —(CH$_2$)$_{0-2}$SH, —(CH$_2$)$_{0-2}$NH$_2$, —(CH$_2$)$_{0-2}$NHR$^•$, —(CH$_2$)$_{0-2}$NR$^•$$_2$, —NO$_2$, —SiR$^•$$_3$, —OSiR$^•$$_3$, —C(O)SR$^•$, —(C$_{1-4}$ straight or branched alkylene)C(O)OR$^•$, or —SSR$^•$ wherein each R$^•$ is unsubstituted or where preceded by "halo" is substituted only with one or more halogens, and is independently selected from C$_{1-4}$ aliphatic, —CH$_2$Ph, —O(CH$_2$)$_{0-1}$ Ph, or a 5- to 6-membered saturated, partially unsaturated, or aryl ring having 0-4 heteroatoms independently selected from nitrogen, oxygen, or sulfur. Suitable divalent substituents on a saturated carbon atom of R° include ═O and ═S.

Suitable divalent substituents on a saturated carbon atom of an "optionally substituted" group include the following: ═O, ═S, ═NNR*$_2$, ═NNHC(O)R*, ═NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5- to 6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5- to 6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3- to 12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —P(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur.

The term "carbohydrate" refers to a sugar or polymer of sugars. The terms "saccharide", "polysaccharide", "carbohydrate", and "oligosaccharide", may be used interchangeably. Most carbohydrates are aldehydes or ketones with many hydroxyl groups, usually one on each carbon atom of the molecule. Carbohydrates generally have the molecular formula C$_n$H$_{2n}$O$_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose. (e.g., 2'-fluororibose, deoxyribose, and hexose). Carbohydrates may exist in many different forms, for example, conformers, cyclic forms, acyclic forms, stereoisomers, tautomers, anomers, and isomers.

The term "polypeptide," generally speaking, is a string of at least two amino acids attached to one another by a peptide bond. In some embodiments, a polypeptide includes at least 3-5 amino acids, each of which is attached to others by way of at least one peptide bond. Those of ordinary skill in the art will appreciate that polypeptides sometimes include "unnatural" amino acids or other entities that nonetheless are capable of integrating into a polypeptide chain, optionally. The term "peptide" is generally used to refer to a polypeptide having a length of less than about 100 amino acids.

As used herein, the phrase "unnatural amino acid" refers to amino acids not included in the list of 20 amino acids naturally occurring in proteins. Such amino acids include the D-isomer of any of the 20 naturally occurring amino acids. Unnatural amino acids also include homoserine, ornithine, norleucine, and thyroxine. Other unnatural amino acids side-chains are well known to one of ordinary skill in the art and include unnatural aliphatic side chains. Other unnatural amino acids include modified amino acids, including those that are N-alkylated, cyclized, phosphorylated, acetylated, amidated, azidylated, labelled, and the like. In some embodiments, an unnatural amino acid is a D-isomer. In some embodiments, an unnatural amino acid is a L-isomer.

As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, etc. In some embodiments, proteins may comprise natural amino acids, non-natural amino acids, synthetic amino acids, and combinations thereof.

The term "suitable organic group," as used herein, refers to a protein, peptide, carbohydrate, aliphatic, aryl, heteroaliphatic, heteroaryl, or acyl group.

As used herein, the term "polyol" refers to compounds with multiple hydroxyl functional groups. In some embodiments, a polyol is a diol, triol, or tetrol. In some embodiments, a polyol is an alkylene glycol. In some embodiments, a polyol is an alkylene triol.

As used herein, the term "hydrogel" refers to a polymeric material, typically a network or matrix of polymer chains, capable of swelling in water or becoming swollen with water. Such polymeric material already swollen or partially swollen with water may also be called a hydrogel. A hydrogel network or matrix may or may not be cross-linked, and cross-linked materials may be physically and/or chemically cross-linked. Hydrogels also include polymeric materials that are water swellable and/or water swelled. A hydrogel may exist in various states of hydration. In some embodiments, a hydrogel is unhydrated. In some embodiments, a hydrogel is partially hydrated. In some embodiments, a hydrogel is fully hydrated. In certain embodiments, a hydrogel may be described as being swollen with water. In certain embodiments, a hydrogel may be described as being water swellable.

As used herein, the term "seroma" refers to an accumulation of serous serum in a wound bed or surgical site. While a seroma may be infected or comprise infected tissue, a seroma does not necessarily involve the presence of white blood cells, bacteria, and the breakdown products of both.

As used herein, the term "hemostasis" refers to the action of stopping or reducing bleeding (e.g., of or in a tissue). The tissue may be any biological tissue. In some embodiments, the tissue is living animal tissue. In some embodiments, the tissue is in and/or around a wound bed. In some embodiments, the tissue is in and/or around a surgical site.

As used herein, the term "surgical site" refers to the tissues of a surgical patient adjacent to an actual or intended surgical action during or subsequent to a surgery. In some embodiments, a surgical site is a skin surface location at which surgery is being or has been conducted. A surgical site includes the intended site for surgical incision as well as wounds to the skin, such as puncture wounds by objects. In some embodiments, a surgical site includes a peripheral area extending from immediately adjacent the surgical site up to about 30 cm from the surgical site. In some embodiments, a surgical site includes a peripheral area extending from about 3 cm to about 30 cm from the surgical site.

The term "incision" or "surgical incision" refers to any surgical penetration which extends beyond the epidermal or dermal layer of a patient's skin and includes, by way of example, incisions or punctures made by needles, knives (including surgical knives and surgical cautery knives), medical lasers, trocars, and punctures (e.g., those resulting from IV, blood transfusion/donation, vaccine inoculation, medicament injections, hemodialysis, etc.).

The term "wound" refers to any wound or injury, including surgically created wounds and accidental or traumatic wounds, such as compound fractures, gunshot wounds, knife wounds, pellet wounds, contaminated or infected wounds. The term "wound bed" may be used interchangeably with "wound." In some embodiments, a wound includes a peripheral area extending from immediately adjacent the wound up to about 30 cm from the wound. In some embodiments, a wound includes a peripheral area extending from about 3 cm to about 30 cm from the wound.

As used herein, the term "subject" or "patient" refers to any organism to which a composition of this invention may be administered, e.g., for experimental, diagnostic, prophylactic, and/or therapeutic purposes. Typical subjects include animals (e.g., mammals such as mice, rats, dogs, cats, rabbits, non-human primates, and humans).

An individual who is "suffering from" a disease, disorder, and/or condition has been diagnosed with or displays one or more symptoms of the disease, disorder, and/or condition.

An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition. In some embodiments, an individual who is susceptible to a disease, disorder, and/or condition is an individual having higher risk (typically based on genetic predisposition, environmental factors, personal history, or combinations thereof) of developing a particular disease or disorder, or symptoms thereof, than is observed in the general population.

The term "treatment" is used herein to characterize a method or process that is aimed at (1) delaying or preventing the onset of a disease, disorder, and/or condition; (2) slowing down or stopping the progression, aggravation, or deterioration of one or more symptoms of the disease, disorder, and/or condition; (3) bringing about ameliorations of the symptoms of the disease, disorder, and/or condition; (4) reducing the severity or incidence of the disease, disorder, and/or condition; and/or (5) curing the disease, disorder, and/or condition. A treatment may be administered prior to the onset of the disease, disorder, and/or condition, for a prophylactic or preventive action. Alternatively or additionally, the treatment may be administered after initiation of the disease, disorder, and/or condition, for a therapeutic action.

The term "palliative" refers to treatment that is focused on the relief of symptoms of a disease and/or side effects of a therapeutic regimen, but is not curative.

As used herein and in the claims, the singular forms "a", "an", and "the" include the plural reference unless the context clearly indicates otherwise. Thus, for example, a reference to "a compound" includes a plurality of such compounds. Similarly, a reference to "a polymer" includes a plurality of such polymers.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle, such as a liquid or solid filler, diluent, excipient, or solvent encapsulating material, involved in carrying or transporting the subject compound. Each carrier must be "acceptable" in the sense of being compatible with the subject compound and other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

DETAILED DESCRIPTION OF CERTAIN EMBODIMENTS

Polymeric biomaterials have contributed significantly to the advancement of medical and surgical practice over the past few decades. Their macromolecular structure can be tailored to provide the appropriate combination of chemical, physical, and biological properties necessary for a range of medical and surgical applications. The rational design of polymeric biomaterials has impacted many fields including drug and gene delivery, orthopedics, tissue engineering, ophthalmology, and general surgery (Langer, R., Tirrell, D. A. (2004) "Designing materials for biology and medicine." *Nature* 428, 487-492; Putnam, D. (2006) "Polymers for gene delivery across length scales." *Nature Materials* 5, 439-451; Wong, S. Y., Pelet, J. M., Putnam, D. (2007) "Polymer systems for gene delivery-past, present, and future." *Prog Polym Sci* 32, 799-837).

The present disclosure encompasses the recognition that polymeric biomaterials can be useful in the treatment of wounds and postoperative surgical sites. To Applicants' knowledge, there are only two published accounts of synthetic biomaterials for seroma prevention. Silverman et al. reported a photopolymerizable material that effectively reduced seroma in a rat mastectomy model, but no follow on studies have been reported (Silverman, R. P., et al. (1999) "Transdermal photopolymerized adhesive for seroma prevention." *Plast Reconstr Surg* 103, 531-535). Rubin and co-workers have developed a urethane-based material that shows efficacy in a dog seroma model. However, while the results are promising, the material requires long cure times and appears to be only slowly degradable (Gilbert, T. et al. (2008) "Lysine-derived urethane surgical adhesive prevents seroma formation in a canine abdominoplasty model." *Plast. Reconstr. Surg* 122, 95-102). Given that seromas cause significant patient morbidity, it is interesting they have not received more attention from the biomaterials community.

The present disclosure provides, among other things, new surgical biomaterials with adjustable physiochemical properties that are biocompatible, easy to handle and apply, and useful for treating postoperative conditions and/or complications. Such materials include copolymers whose physical and rheological properties can be fine-tuned by adjusting the length of its constituting blocks. In certain embodiments, provided surgical biomaterials are useful in treating seromas, tissue adhesion, and/or bleeding.

Applicants previously described the successful synthesis and characterization of a diblock copolymer, MPEG-pDHA, comprised of a monomethoxy poly(ethylene glycol) (MPEG) block, and a polycarbonate (pDHA) block based on the metabolic intermediate, dihydroxyacetone (DHA). See Zawaneh, P. N., Doody, A. M., Zelikin, A. N., Putnam, D. (2006) "Diblock copolymers based on dihydroxyacetone and ethylene glycol: Synthesis, characterization, and nanoparticle formulation." *Biomacromolecules* 7, 3245-3251; and U.S. Pat. Application Publication No. 2008-0194786, the entire contents of each of which are hereby incorporated by reference.

Subsequent work with pDHA copolymers has revealed that such copolymers have medically useful properties. Furthermore, Applicants have unexpectedly found that at higher concentrations, pDHA copolymers form a physically cross-linked hydrogel that possesses properties that differ from non-physically cross-linked, non-hydrogel compositions. In certain embodiments, provided pDHA copolymers are thixotropic. In certain embodiments, provided pDHA copolymers display rapid chain relaxation. In certain embodiments, provided pDHA copolymers possess high porosity. In certain embodiments, provided pDHA copolymers possess high water content. In certain embodiments, provided pDHA copolymers are injectable. In certain embodiments, a provided pDHA copolymer is a powder.

Applicants have found that by controlling the concentration and composition of provided copolymers, physically cross-linked hydrogels are formed. In certain embodiments, provided copolymers possess desirable characteristics (for example, physically entangled networks that form physical cross-links) for uses as described herein. In some embodiments, such characteristics are not present at low concentrations of provided copolymers. In some embodiments, characteristics such as hydrogel formation are present at high concentrations of provided copolymers. In some embodiments, provided copolymer form nanoparticles at low concentrations.

In some embodiments, the present disclosure provides methods of making provided hydrogel compositions.

In certain embodiments, the present disclosure provides copolymers comprising poly-dihydroxyacetone (pDHA). In some embodiments, provided copolymers are block copolymers of pDHA. In some embodiments, provided copolymers are diblock copolymers of pDHA. In some embodiments, provided copolymers are triblock copolymers of pDHA. In some embodiments, provided copolymers are quadblock copolymers of pDHA. In some embodiments, provided copolymers are multiblock copolymers of pDHA. In some embodiments, provided copolymers comprise DHA and at least one other monomer. In some embodiments, provided copolymers comprise DHA and glycerol. In some embodiments, provided copolymers comprise DHA and an alkylene glycol. In some embodiments, provided copolymers comprise DHA and PEG. In some embodiments, provided copolymers are PEG-pDHA diblock copolymers. In some embodiments, a provided pDHA copolymer is poly(MPEG-b-2-oxypropylene carbonate).

In some embodiments, provided copolymers comprise DHA and a polyol. In some embodiments, a polyol is selected from the group consisting of ethylene glycol, propylene glycol (i.e., a polymer comprising 1,2-propane diol, 2-methyl-1,3-propanediol, or 1,3-propane diol), butylene glycol (i.e., a polymer comprising 1,2-butanediol, 1,2-butanediol, or 1,4-butanediol), and a carbohydrate. In some embodiments, a carbohydrate polyol is a cyclic saccharide. In some embodiments, a carbohydrate polyol is a hydrogenated sugar alcohol.

In some embodiments, provided copolymers are terminated with a suitable organic group. In certain embodiments, an alkylene glycol block of a provided copolymer is terminated with a suitable organic group. In some embodiments, suitable organic groups are aliphatic, acyl, heteroaliphatic, aryl, or heteroaryl. In some embodiments, a suitable organic group is a carbohydrate, a protein, or a peptide.

In some embodiments, provided pDHA copolymers are block copolymers. In some embodiments, provided pDHA copolymers are random copolymers.

In some embodiments, provided copolymers comprise DHA, glycerol, and PEG. In some embodiments, a provided pDHA copolymer comprises a first block of PEG and a second block comprising DHA and glycerol. In some embodiments, the second block comprising DHA and glycerol is a block copolymer. In some embodiments, the second block comprising DHA and glycerol is a random copolymer.

In certain embodiments, provided pDHA copolymers are poly(alkylene glycol)-pDHA diblock copolymers. In certain embodiments, provided pDHA copolymers are poly(ethylene glycol)-pDHA diblock copolymers. In certain embodiments, provided pDHA copolymers are poly(propylene glycol)-pDHA diblock copolymers. In certain embodiments, provided pDHA copolymers are poly(glycerol)-pDHA diblock copolymers.

In certain embodiments, a poly(alkylene-glycol) block of a provided copolymer is linear. In other embodiments, a poly(alkylene-glycol) block of a provided copolymer is branched. In certain embodiments, a PEG block of a provided copolymer is branched. In certain embodiments, a PEG block of a provided copolymer is a comb PEG. In certain embodiments, a PEG block of a provided copolymer is a star PEG. In some embodiments, a branched PEG block comprises 3 to 200 PEG chains emanating from a central core group. In some embodiments, a branched PEG block comprises 3 to 100 PEG chains emanating from a central core group. In some embodiments, a branched PEG block comprises 3 to 50 PEG chains emanating from a central core group. In some embodiments, a branched PEG block comprises 3 to 40 PEG chains emanating from a central core group. In some embodiments, a branched PEG block comprises 3 to 30 PEG chains emanating from a central core group. In some embodiments, a branched PEG block comprises 3 to 20 PEG chains emanating from a central core group. In some embodiments, a branched PEG block comprises 10 PEG chains emanating from a central core group. In some embodiments, a branched PEG block comprises 9 PEG chains emanating from a central core group. In some embodiments, a branched PEG block comprises 8 PEG chains emanating from a central core group. In some embodiments, a branched PEG block comprises 7 PEG chains emanating from a central core group. In some embodiments, a branched PEG block comprises 6 PEG chains emanating from a central core group. In some embodiments, a branched PEG block comprises 5 PEG chains emanating from a central core group. In some embodiments, a branched PEG block comprises 4 PEG chains emanating from a central core group. In some embodiments, a branched PEG block comprises 3 PEG chains emanating from a central core group.

In certain embodiments, a pDHA block of provided copolymers has a $M_w$ from about 100 to about 1,000,000 daltons. In certain embodiments, a pDHA block of provided copolymers has a $M_w$ from about 1,000 to about 1,000,000 daltons. In certain embodiments, a pDHA block of provided copolymers has a $M_w$ from about 10,000 to about 1,000,000 daltons. In certain embodiments, a pDHA block of provided copolymers has a $M_w$ from about 100,000 to about 1,000,000 daltons. In certain embodiments, a pDHA block of provided copolymers has a $M_w$ from about 100 to about 100,000 daltons. In certain embodiments, a pDHA block of provided copolymers has a $M_w$ from about 100 to about 50,000 daltons. In certain embodiments, a pDHA block of provided copolymers has a $M_w$ from about 100 to about 10,000 daltons. In certain embodiments, a pDHA block of provided copolymers has a $M_w$ from about 1,000 to about 50,000 daltons. In certain embodiments, a pDHA block of provided copolymers has a $M_w$ from about 1,000 to about 10,000 daltons. In certain embodiments, a pDHA block of provided copolymers has a $M_w$ from about 1,000 to about 5,000 daltons. In certain embodiments, a pDHA block of provided copolymers has a $M_w$ from about 2,000 to about 5,000 daltons. In certain embodiments, a pDHA block of provided copolymers has a $M_w$ from about 2,000 to about 4,000 daltons. In certain embodiments, a pDHA block of provided copolymers has a $M_w$ from about 2,500 to about 4,000 daltons. In certain embodiments, a pDHA block of provided copolymers has a $M_w$ from about 2,500 to about 3,500 daltons. In certain embodiments, a pDHA block of provided copolymers has a $M_w$ of about 3,000 daltons.

In certain embodiments, a non-DHA polyol block of provided copolymers has a $M_w$ from about 100 to about 1,000,000 daltons. In certain embodiments, a non-DHA polyol block of provided copolymers has a $M_w$ from about 1,000 to about 1,000,000 daltons. In certain embodiments, a non-DHA polyol block of provided copolymers has a $M_w$ from about 10,000 to about 1,000,000 daltons. In certain embodiments, a non-DHA polyol block of provided copolymers has a $M_w$ from about 100,000 to about 1,000,000 daltons. In certain embodiments, a non-DHA polyol block of provided copolymers has a $M_w$ from about 100 to about 100,000 daltons. In certain embodiments, a non-DHA polyol block of provided copolymers has a $M_w$ from about 100 to about 50,000 daltons. In certain embodiments, a non-DHA polyol block of provided copolymers has a $M_w$ from about 100 to about 10,000 daltons. In certain embodiments, a non-DHA polyol block of provided copolymers has a $M_w$ from about 1,000 to about 50,000 daltons. In certain embodiments, a non-DHA polyol block of provided copolymers has a $M_w$ from about 1,000 to about 10,000 daltons. In certain embodiments, a non-DHA polyol block of provided copolymers has a $M_w$ from about 1,000 to about 5,000 daltons. In certain embodiments, a non-DHA polyol block of provided copolymers has a $M_w$ from about 2,000 to about 5,000 daltons. In certain embodiments, a non-DHA polyol block of provided copolymers has a $M_w$ from about 3,000 to about 6,000 daltons. In certain embodiments, a non-DHA polyol block of provided copolymers has a $M_w$ from about 2,500 to about 4,000 daltons. In certain embodiments, a non-DHA polyol block of provided copolymers has a $M_w$ from about 2,500 to about 3,500 daltons. In certain embodiments, a non-DHA polyol block of provided copolymers has a $M_w$ of about 5,000 daltons.

In certain embodiments, a provided copolymer is a hydrogel. In some embodiments, a provided copolymer is not cross-linked. In some embodiments, a provided copolymer is cross-linked. In some embodiments, a provided copolymer has the property of decreasing viscosity with increasing shear rate. In some embodiments, a provided hydrogel has a weight gain swelling percentage of about 100% to about 2,000%. In some embodiments, a provided hydrogel has a weight gain swelling percentage of about 200% to about 1,000%. In some embodiments, a provided hydrogel has a weight gain swelling percentage of about 200% to about 800%. In some embodiments, a provided hydrogel has a weight gain swelling percentage of about 300% to about 700%. In some embodiments, a provided hydrogel has a weight gain swelling percentage of about 400% to about 600%. In some embodiments, a provided hydrogel has a weight gain swelling percentage of about 500% to about 600%.

In some embodiments, a provided copolymer has an entanglement density of about $5 \times 10^{22}$ m$^{-3}$ to about $5 \times 10^{26}$ m$^{-3}$. In some embodiments, a provided copolymer has an entanglement density of about $5 \times 10^{23}$ m$^{-3}$ to about $1 \times 10^{25}$ m$^{-3}$. In some embodiments, a provided copolymer has an entanglement density of about $5 \times 10^{24}$ m$^{-3}$ to about $5 \times 10^{25}$ m$^{-3}$. In some embodiments, a provided copolymer has an entanglement density of about $1 \times 10^{24}$ m$^{-3}$ to about $5 \times 10^{24}$ m$^{-3}$. In some embodiments, a provided copolymer has an entanglement density of about $5 \times 10^{24}$ m$^{-3}$.

In certain embodiments, a provided copolymer has a relaxation time of about 30 to about 1000 seconds. In certain embodiments, a provided copolymer has a relaxation time of about 100 to about 500 seconds. In certain embodiments, a provided copolymer has a relaxation time of about 200 to about 500 seconds. In certain embodiments, a provided copolymer has a relaxation time of about 200 to about 400 seconds. In certain embodiments, a provided copolymer has a relaxation time of about 200 to about 350 seconds. In certain embodiments, a provided copolymer has a relaxation time of about 225 to about 275 seconds. In certain embodiments, a provided copolymer has a relaxation time of about 250 seconds.

Dihydroxyacetone is known to react with amino acids in the upper layers of the skin to produce a tanning effect. The product of DHA-skin protein reactions is therefore proteins functionalized with monomeric DHA, not polymeric DHA. In certain embodiments, provided pDHA copolymers do not comprise DHA-protein conjugates formed by a Maillard reaction (i.e., reaction between a reducing sugar and an amino acid).

In certain embodiments, a provided pDHA copolymer is of formula VII-a:

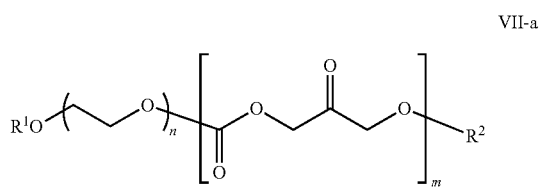

VII-a wherein,
$R^1$ and $R^2$ are each independently an optionally substituted group selected from $C_{1-20}$ aliphatic; a 3- to 7-membered saturated or partially unsaturated monocyclic carbocyclic ring; a 7- to 10-membered saturated or partially unsaturated bicyclic carbocyclic ring; phenyl; an 8- to 10-membered bicyclic aryl ring; a 3- to 7-membered saturated or partially unsaturated monocyclic heterocyclic ring having 1-2 heteroatoms independently selected from nitrogen, oxygen, or sulfur; a 7- to 10-membered saturated or partially unsaturated bicyclic heterocyclic ring having 1-3 heteroatoms independently selected from nitrogen, oxygen, or sulfur; an 8- to 10-membered bicyclic aryl ring; a 5- to 6-membered heteroaryl ring having 1-3 heteroatoms independently selected from nitrogen, oxygen, or sulfur; or an 8- to 10-membered bicyclic heteroaryl ring having 1-4 heteroatoms independently selected from nitrogen, oxygen, or sulfur; and
n and m each independently range from 1 to 2000.

In certain embodiments, $R^1$ is $C_{1-20}$ aliphatic. In certain embodiments, $R^1$ is $C_{1-10}$ aliphatic. In certain embodiments, $R^1$ is $C_{1-6}$ aliphatic. In certain embodiments, $R^1$ is methyl. In some embodiments, $R^1$ is a suitable organic group. In some embodiments, $R^1$ is selected from the group consisting of carbohydrates, proteins, and peptides.

In some embodiments, $R^2$ is $C_{1-20}$ aliphatic. In certain embodiments, $R^2$ is $C_{1-10}$ aliphatic. In certain embodiments, $R^2$ is $C_{1-6}$ aliphatic. In certain embodiments, $R^2$ is methyl.

In some embodiments, n is from 1-2000. In some embodiments, n is from 10-1000. In some embodiments, n is from 10-500. In some embodiments, n is from 10-250. In some embodiments, n is from 10-200. In some embodiments, n is from 10-150. In some embodiments, n is from 50-200. In some embodiments, n is from 75-125. In some embodiments, n is a number such that the total molecular weight of the n bracketed block is from about 200 to about 20,000 daltons. In some embodiments, n is a number such that the total molecular weight of the n bracketed block is from about 500 to about 10,000 daltons. In some embodiments, n is a number such that the total molecular weight of the n bracketed block is from about 1,000 to about 10,000 daltons. In some embodiments, n is a number such that the total molecular weight of the n bracketed block is from about 2,000 to about 10,000 daltons. In some embodiments, n is a number such that the total molecular weight of the n bracketed block is from about 3,000 to about 6,000 daltons.

In some embodiments, m is from 1-2000. In some embodiments, m is from 2-2000. In some embodiments, m is from 5-1000. In some embodiments, m is from 5-500. In some embodiments, m is from 5-250. In some embodiments, m is from 5-200. In some embodiments, m is from 5-100. In some embodiments, m is from 15-50. In some embodiments, m is from 20-30. In some embodiments, m is a number such that the total molecular weight of the m bracketed block is from about 200 to about 20,000 daltons. In some embodiments, m is a number such that the total molecular weight of the m bracketed block is from about 500 to about 10,000 daltons. In some embodiments, m is a number such that the total molecular weight of the m bracketed block is from about 1,000 to about 10,000 daltons. In some embodiments, m is a number such that the total molecular weight of the m bracketed block is from about 2,000 to about 8,000 daltons. In some embodiments, m is a number such that the total molecular weight of the m bracketed block is from about 3,000 to about 7,000 daltons. In some embodiments, m is a number such that the total molecular weight of the m bracketed block is from about 4,000 to about 6,000 daltons. In some embodiments, m is a number such that the total molecular weight of the m bracketed block is about 5,000 daltons.

In some embodiments, molecular weights described herein refer to the molecular weight of a single molecule or part of a molecule. In some embodiments, molecular weights described herein refer to the average molecular weight in a composition of provided polymers.

In certain embodiments, a provided pDHA copolymer is of formula VII-b:

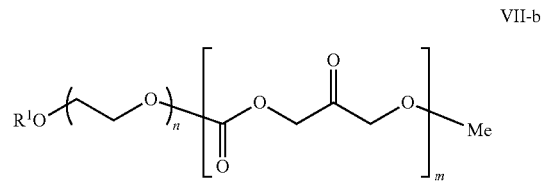

VII-b wherein each of $R^1$, n, and m are as defined above and described in classes and subclasses herein.

It will be appreciated that provided pDHA copolymers comprise a ketone group that may be protected with a carbonyl protecting group. For example, provided polymers can be made using dihydroxyacetone monomer and/or dimer that are chemically protected, e.g., from protected dihydroxyacetone monomer where the carbonyl group of the monomer is protected, e.g., from 2,2-di-$C_1$-$C_{10}$ alkoxypropane-1,3-diol, or from 2,2-dimethoxy-propane-1,3-diol. Other protected forms of the starting material include those where the carbonyl group of the monomer is protected with methoxybenzyl, benzyloxy, or allyloxy, or those where the hydroxyl groups of the dimer are protected, e.g., from 2,5-di-$C_1$-$C_{10}$ alkoxy-2,5-bis(hydroxymethyl)-[1,4]-dioxane. The 2,2-dimethoxy-propane-1,3 diol is readily made from combination of DHA monomer and dimer as described in Ferroni, E. L., et al, *J. Org. Chem* 64, 4943-4945 (1999).

In addition to polymerizing functionalized monomer, provided pDHA copolymers may be functionalized at the polymer stage. Such functionalization has been previously demonstrated in the art (see for example U.S. Pat. Application Publication No. 2008-0194786). For example, a compound of formula VII-a may be functionalized by one or more nucleophiles. In certain embodiments, a compound of formula VII-a is treated with an amine and a suitable reducing agent. In some embodiments, the reducing agent is selected from $NaBH_4$, $NaBH_3CN$, or $NaBH(OCOCH_3)_3$.

Thus, in certain embodiments, provided pDHA copolymers are of formula VIII:

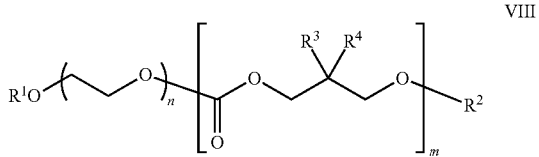

VIII wherein each of $R^1$, $R^2$, n, and m is as defined above and described in classes and subclasses herein; and $R^3$ and $R^4$ are each independently selected from the group consisting of $R^5$, $—OR^5$, and $—N(R^5)_2$; or:

$R^3$ and $R^4$ are optionally taken together with their intervening atoms to form an optionally substituted ring selected from a 3- to 7-membered saturated or partially unsaturated monocyclic heterocyclic ring having 1-2 heteroatoms independently selected from nitrogen, oxygen, or sulfur; or a 7- to 10-membered saturated or partially unsaturated bicyclic heterocyclic ring having 1-3 heteroatoms independently selected from nitrogen, oxygen, or sulfur; and each $R^5$ is independently hydrogen or an optionally substituted group selected from $C_{1-20}$ aliphatic; a 3- to 7-membered saturated or partially unsaturated monocyclic carbocyclic ring; a 7- to 10-membered saturated or partially unsaturated bicyclic carbocyclic ring; phenyl; an 8- to 10-membered bicyclic aryl ring; a 3- to 7-membered saturated or partially unsaturated monocyclic heterocyclic ring having 1-2 heteroatoms independently selected from nitrogen, oxygen, or sulfur; a 7- to 10-membered saturated or partially unsaturated bicyclic heterocyclic ring having 1-3 heteroatoms independently selected from nitrogen, oxygen, or sulfur; an 8- to 10-membered bicyclic aryl ring; a 5- to 6-membered heteroaryl ring having 1-3 heteroatoms independently selected from nitrogen, oxygen, or sulfur; or an 8- to 10-membered bicyclic heteroaryl ring having 1-4 heteroatoms independently selected from nitrogen, oxygen, or sulfur.

In some embodiments, $R^3$ is $R^5$. In some embodiments, $R^3$ is $—OR^5$. In other embodiments, $R^3$ is $—N(R^5)_2$. In some embodiments, $R^3$ is $—N(R^5)_2$, wherein each $R^5$ is independently an optionally substituted group selected from $C_{1-10}$ aliphatic or phenyl. In some embodiments, $R^3$ is $—NH(CH_2)_4 CH(NH_2)CO_2H$.

In some embodiments, $R^4$ is $R^5$. In some embodiments, $R^4$ is $—OR^5$. In other embodiments, $R^4$ is $—N(R^5)_2$.

In certain embodiments, $R^3$ and $R^4$ form a suitable carbonyl protecting group. Suitable carbonyl protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference.

In some embodiments, $R^3$ and $R^4$ are each independently selected from the group consisting of $R^5$, $—OR^5$, and $—N(R^5)_2$. In certain embodiments, $R^3$ and $R^4$ are each $—N(R^5)_2$, wherein $R^5$ is $C_{1-20}$ aliphatic. In certain embodiments, $R^3$ and $R^4$ are each $—OR^5$, wherein $R^5$ is $C_{1-20}$ aliphatic. In certain embodiments, $R^3$ and $R^4$ are each $—OR^5$, wherein $R^5$ is $C_{1-10}$ aliphatic. In certain embodiments, $R^3$ and $R^4$ are each $—OR^5$, wherein $R^5$ is $C_{1-6}$ aliphatic. In certain embodiments, $R^3$ and $R^4$ are each $—OR^5$, wherein $R^5$ is ethyl. In certain embodiments, $R^3$ and $R^4$ are each $—OR^5$, wherein $R^5$ is methyl.

In some embodiments, $R^3$ and $R^4$ are taken together with their intervening atoms to form an optionally substituted spirocyclic 3- to 7-membered saturated or partially unsaturated monocyclic heterocyclic ring having 1-2 heteroatoms independently selected from nitrogen, oxygen, or sulfur. In some embodiments, $R^3$ and $R^4$ are taken together with their intervening atoms to form an optionally substituted 5- to 6-membered cyclic ketal. In some embodiments, $R^3$ and $R^4$ are not taken together with their intervening atoms to form an optionally substituted 5- to 6-membered cyclic ketal.

In certain embodiments, $R^5$ is hydrogen. In certain embodiments, $R^5$ is $C_{1-20}$ aliphatic. In certain embodiments, $R^5$ is a 3- to 7-membered saturated or partially unsaturated monocyclic carbocyclic ring. In certain embodiments, $R^5$ is a 7- to 10-membered saturated or partially unsaturated bicyclic carbocyclic ring. In certain embodiments, $R^5$ is phenyl. In certain embodiments, $R^5$ is an 8- to 10-membered bicyclic aryl ring. In certain embodiments, $R^5$ is a 3- to 7-membered saturated or partially unsaturated monocyclic heterocyclic ring having 1-2 heteroatoms independently selected from nitrogen, oxygen, or sulfur. In certain embodiments, $R^5$ is a 7- to 10-membered saturated or partially unsaturated bicyclic heterocyclic ring having 1-3 heteroatoms independently selected from nitrogen, oxygen, or sulfur. In certain embodiments, $R^5$ is an 8- to 10-membered bicyclic aryl ring. In certain embodiments, $R^5$ is a 5- to 6-membered heteroaryl ring having 1-3 heteroatoms independently selected from nitrogen, oxygen, or sulfur. In certain embodiments, $R^5$ is an 8- to 10-membered bicyclic heteroaryl ring having 1-4 heteroatoms independently selected from nitrogen, oxygen, or sulfur.

In certain embodiments, a provided pDHA copolymers are of formula IX:

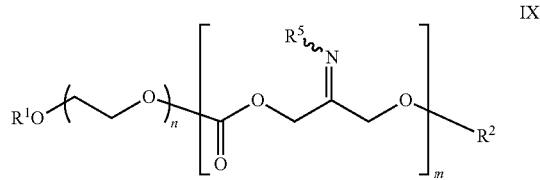

IX wherein each of $R^1$, $R^2$, $R^5$, n, and m is as defined above and described in classes and subclasses herein.

In certain embodiments, a provided pDHA copolymer comprises a repeating subunit:

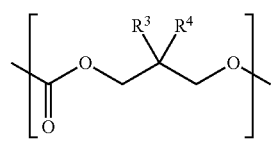

wherein each of $R^3$ and $R^4$ is as defined above and described in classes and subclasses herein.

In certain embodiments, a provided pDHA copolymer comprises a repeating subunit:

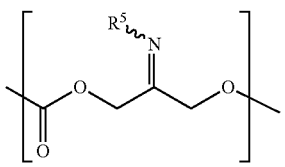

wherein $R^5$ is as defined above and described in classes and subclasses herein.

In certain embodiments, a provided pDHA copolymer is poly(MPEG-b-2-oxypropylene carbonate). In certain embodiments, a provided pDHA copolymer is poly(MPEG-b-2,2,di($C_{1-12}$ aliphatic)oxy-1,3-propylene carbonate). In certain embodiments, a provided pDHA copolymer is poly(MPEG-b-2,2,dimethyoxy-1,3-propylene carbonate).

MPEG-pDHA Copolymer

As described above, the present disclosure provides pDHA copolymers and uses thereof. In some embodiments, provided diblock copolymers comprise monomethoxy-polyethylene glycol and a polycarbonate based on the human metabolite, dihydroxyacetone.

Polyethylene glycol (PEG) based polymers have received considerable attention as biomaterials owing to PEG's favorable chemical and biological properties, particularly its established biocompatibility and low immunogenicity (Hubbell, J. A. (1998) "Synthetic biodegradable polymers for tissue engineering and drug delivery." *Curr Opin Solid St Mat Sci* 3, 246-251). DHA is a three carbon ketose that is an intermediate metabolite in the glycolysis pathway, making it a promising building block for new biomaterials (Mathews, C., Van Holde, K. (1996) *Biochemistry* (The Benjamin/Cummings Publishing Co, Menlo Park, Calif.)). Additionally, DHA is readily manufactured as a fermentative product from corn syrup and methanol (Kato, N., Kobayashi, H., Shimao, M., Sakazawa, C. (1986) "Dihydroxyacetone production from methanol by a dihydroxyacetone kinase deficient mutant of *hansenula-polymorpha*." *Appl Microbiol Biot* 23, 180-186). It is currently used as the active ingredient in sunless tanning lotions owing to its ability to form Schiff bases by the reaction of primary amines with its C2 carbonyl (Soler, C., Soley, M. (1993) "Rapid and delayed-effects of epidermal growth-factor on gluconeogenesis." *Biochem J* 294, 865-872; Davis, L. (1973) "Structure of dihydroxyacetone in solution." *Bioorg Chem* 2, 197-201; Nguyen, B. C., Kochevar, I. E. (2003) "Influence of hydration on dihydroxyacetone-induced pigmentation of stratum corneum." *J Invest Dermatol* 120, 655-661). The DHA-based polycarbonate (pDHA) is hydrophilic, but insoluble in water and most common organic solvents, and is also amendable to one step functionalization through reductive amination at the C2 carbonyl group (Zelikin, A. N., Zawaneh, P. N., Putnam, D. (2006) "A functionalizable biomaterial based on dihydroxyacetone, an intermediate of glucose metabolism." *Biomacromolecules* 7, 3239-3244).

In certain embodiments, a provided MPEG-pDHA diblock copolymer captures some of the properties of both its constituting blocks and incorporates them to form a physically cross-linked hydrogel upon hydration. While not wishing to be bound by any particular theory, it is believed that MPEG-pDHA based hydrogels can be injected into the wound bed to act as both a space filler and bioadhesive owing to pDHA's capacity to bind primary amines (Zelikin, supra) allowing the gel to hold the tissue flaps together and seal surrounding leaky blood vessels and lymphatics thereby reducing fluid accumulation.

As described above, the properties and performance of the gel can be controlled by adjusting the length of the polymer's constituting blocks. Experiments are described in the ensuing Examples wherein MPEG-pDHA is synthesized in various molecular weights ($M_w$). In these particular experiments, the MPEG $M_w$ was held constant at 5000 since, at this low $M_w$, it can undergo renal clearance as required by the FDA for approved human uses. The pDHA $M_w$ was varied (3000, 5000, and 7000) to produce the three desired block copolymers (abbreviated as 5000-3000, 5000-5000, and 5000-7000). MPEG is a water soluble hydrophilic polymer, while pDHA is insoluble in water but hydrophilic based on contact angle measurements (Zelikin, supra). These characteristics allow the block copolymers to form nanoparticles at low concentrations in aqueous environments (Zawaneh, supra). The present disclosure finds unexpectedly that, at higher polymer concentrations, the block copolymers form gels with physically entangled networks. While such physical gelation has been observed previously with certain gels of multiblock copolymers in selective solvents (Wang, L. W., Venkatraman, S., Gan, L. H., Kleiner, L. (2005) "Structure formation in injectable poly(lactide-co-glycolide) depots. II. Nature of the gel." *J Biomed Mater Res* 72B, 215-222; Nyrkova, I. A., Khokhlov, A. R., Doi, M. (1993) "Microdomains in Block-Copolymers and Multiplets in Ionomers—Parallels in Behavior." *Macromolecules* 26, 3601-3610; He, X. W., Herz, J., Guenet, J. M. (1988) "Physical gelation of a multiblock copolymer—Effect of copolymer composition." *Macromolecules* 21, 1757-1763; He, X. W., Herz, J., Guenet, J. M. (1989) "Physical gelation of a multiblock copolymer—Effect of solvent type." *Macromolecules* 22, 1390-1397), the processes and/or conditions required to realize hydrogel formation for any given copolymer are not predictable.

It has been previously observed that an increase in the pDHA chain length increases the size of the insoluble pDHA domains that form the physical cross links of the gel, and reduces the relative contribution of the hydrophilic MPEG domain (Wang 2005, supra). While not wishing to be bound by any particular theory, it is believed that the increased pDHA chain length subsequently increases the entanglement density, as shown in Example 1, which in turn influences the gel porosity and water uptake. High water content and increased porosity tend to improve a material's biocompatibility, and can also influence its viscosity and elastic nature (Langer, supra).

In certain embodiments, provided MPEG-pDHA gels exhibit a high water content that decreases with increasing pDHA chain length and entanglement density, as shown in Table 2 of Example 1. For example, the scanning electron micrographs (SEMs) of cryogenically frozen/lyophilized gels shown in FIG. 1 also illustrate a high degree of porosity that decreases with increasing pDHA chain length and entanglement density.

Figure 3:
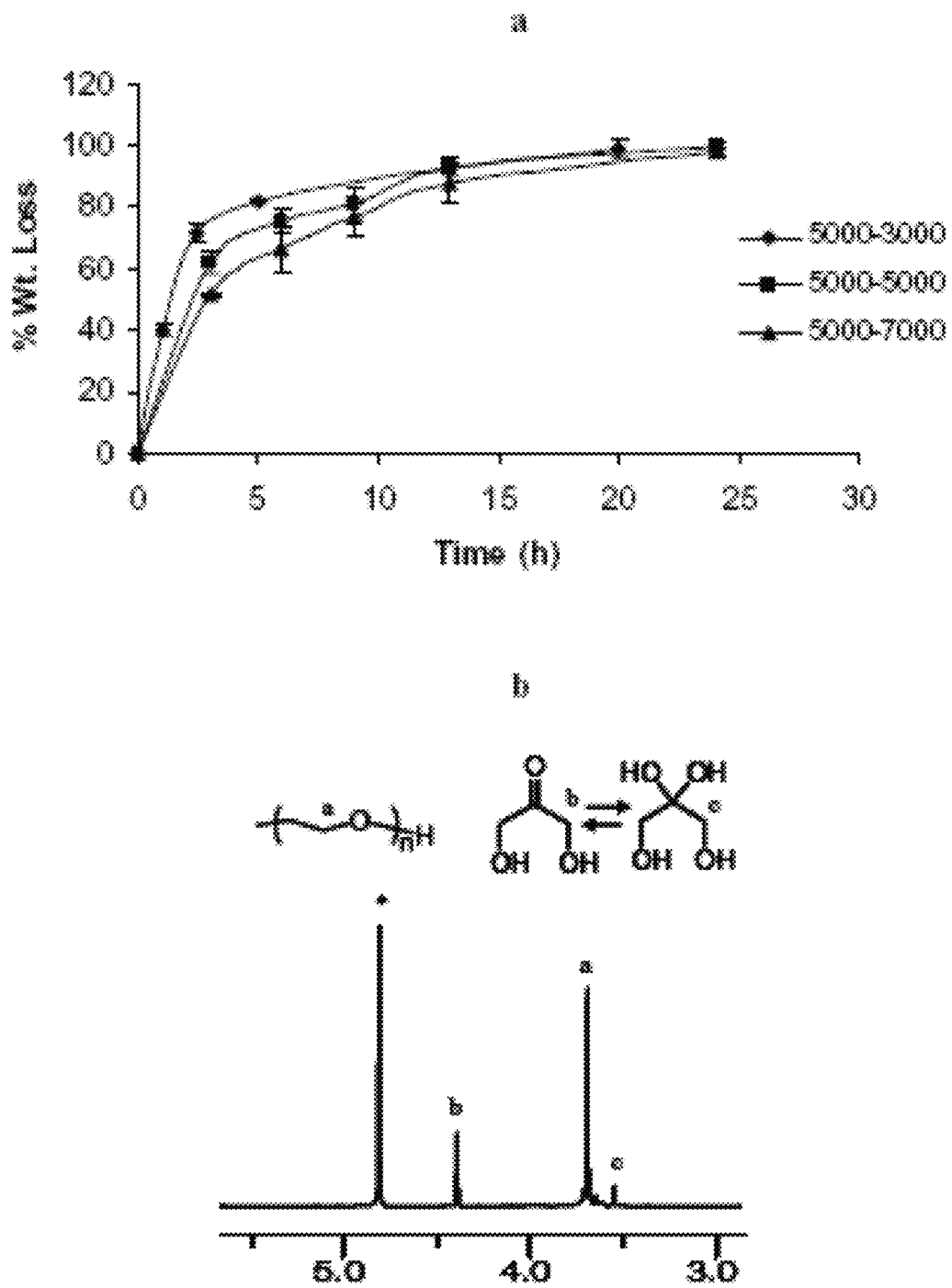
FIG. 3 depicts additional characterization data for MPEG-pDHA. (a) Kinetics of weight loss of MPEG-pDHA hydrogels in water show 100% degradation within one day. (b)$^1$H NMR of hydrolyzed MPEG-pDHA products in $D_2O$, indicate that the end products are MPEG and monomeric DHA.
Figure 11:
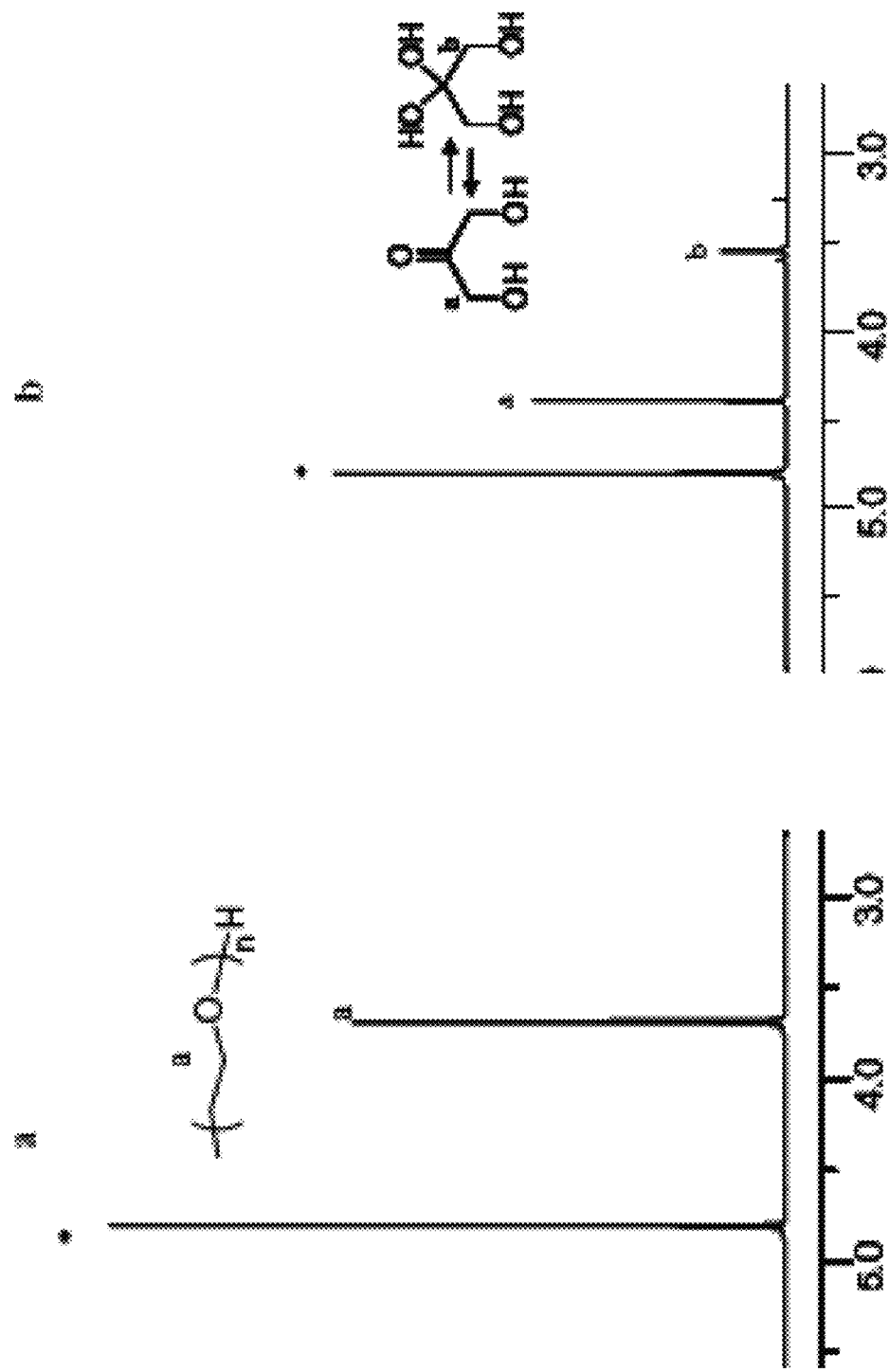
FIG. 11 depicts a $^1$H NMR of (a) MPEG and (b) DHA in $D_2O$*. These spectra and FIG. 3b indicate the degradation products for pDHA hydrogels are MPEG and monomeric DHA.

Two characteristics that may be useful for new biomaterials are the rate of degradation and the composition of the degradation products. Example 2 sets forth in vitro degradation studies performed on certain MPEG-pDHA block copolymers which indicate degradation rates are surprisingly rapid for a polycarbonate and decrease with increasing pDHA block M. In certain embodiments, provided copolymers degrade to completion in 24 hours (FIG. 3a). FIG. 3b is a characteristic $^1H$ NMR of certain block copolymer degradation products, which shows that the soluble polymer degradation products are MPEG, monomeric DHA, and presumably $CO_2$ ($CO_2$ is a common byproduct of polycarbonate degradation) (Tangpasuthadol, V., Pendharkar, S. M., Kohn, J. (2000) "Hydrolytic degradation of tyrosine-derived polycarbonates, a class of new biomaterials. Part I: Study of model compounds." *Biomaterials* 21, 2371-2378; Zhu, K. J., Hendren, R. W., Jensen, K., Pitt, C. G. (1991) "Synthesis, properties, and biodegradation of poly(1,3-Trimethylene Carbonate)." *Macromolecules* 24, 1736-1740). As a reference, FIG. 11 includes $^1$H NMRs of neat MPEG and DHA, respectively. A comparison of FIG. 3 and FIG. 11 shows that the $^1$H NMR peaks overlap, indicating the degradation products of MPEG-pDHA are MPEG and monomeric DHA.

In addition to these in vitro studies, in vivo studies were performed to determine the efficacy of pDHA copolymers in the prevention of postoperative seroma. As described in Example 3, provided pDHA copolymers are effective at significantly decreasing mean seroma volume compared to controls. Given the ease of delivery (injection), compatibility with living tissue and in vivo efficacy, provided copolymers have been demonstrated to be highly effective surgical biomaterials.

Methods of Use

In some embodiments, pDHA copolymers of the present disclosure are provided for use in medicine. In some embodiments, pDHA copolymers of the present disclosure are provided for use in surgery. In certain embodiments, pDHA copolymers of the present disclosure are provided for use in reconstructive surgery. In certain embodiments, pDHA copolymers of the present disclosure are provided for use in the prevention of seroma. In some embodiments, the present disclosure provides methods of using provided pDHA copolymers to eliminate postoperative dead space and reduce seroma formation.

In some embodiments, the present disclosure provides a method of treatment comprising administering a material comprising a poly-dihydroxyacetone (pDHA) copolymer at or near a wound bed or surgical site of a patient. In certain embodiments, the present disclosure provides a method for the prevention or treatment of seromas, the method comprising the step of: administering a material comprising a poly-dihydroxyacetone (pDHA) copolymer at or near a wound bed or surgical site. In certain embodiments, the wound bed or surgical site is in the abdomen.

Seromas

A seroma is an abnormal collection of serous fluid within the tissues of the body, akin to an internal blister. Postoperative accumulations of serous fluid are frequently encountered in patients, particularly when a surgical procedure has required the loosening of relatively large flaps of skin from underlying subcutaneous tissue and deep fascia (e.g., ablative and reconstructive surgeries). Surgeries that require extensive tissue dissection and create large empty spaces can disrupt normal lymphatic flow. Subsequently, transduate fluid collects in these poorly drained "dead spaces" resulting in formation of a seroma (Agrawal, A., Ayantunde, A. A., Cheung, K. L. (2006) "Concepts of seroma formation and prevention in breast cancer surgery." *ANZ J Surg* 76, 1088-1095; Kuroi, K., et al. (2005) "Pathophysiology of seroma in breast cancer." *Breast Cancer* 12, 288-293). Seromas can lead to significant patient morbidity such as infection, decreased limb mobility, and re-operation (Agrawal, supra; Schwabegger, A., Ninkovic, M., Brenner, E., Anderl, H. (1997) "Seroma as a common donor site morbidity after harvesting the latissimus dorsi flap: Observations on cause and prevention." *Ann Plas Surg* 38, 594-597; Budd, D. C., Cochran, R. C., Sturtz, D. L., Fouty, W. J. (1978) "Surgical morbidity after mastectomy operations." *Am J Surg* 135, 218-220). Seroma formation rates range from 9.1 to 81%, depending on the nature of the surgical procedure (Schwabegger, supra; Woodworth, P. A., McBoyle, M. F., Helmer, S. D., Beamer, R. L. (2000) "Seroma formation after breast cancer surgery: Incidence and predicting factors." *Am Surg* 66, 444-450; Roses, D. F., Brooks, A. D., Harris, M. N., Shapiro, R. L., Mitnick, J. (1999) "Complications of level I and II axillary dissection in the treatment of carcinoma of the breast." *Ann Surg* 230, 194-201; Abe, M., Iwase, T., Takeuchi T., Murai H., Miura S. (1998) "A randomized controlled trial on the prevention of seroma after partial or total mastectomy and axillary lymph node dissection." *Breast Cancer* 5, 67-69; Say, C. C., Donegan, W. (1974) "Biostatistical evaluation of complications from mastectomy." *Surg Gynecol Obstet* 138, 370-376; Alvandi, R. Y., Solomon, M. J., Renwick, S. B., Donovan, J. K. (1991) "Preliminary results of conservative treatment of early breast cancer with axillary dissection and post operative radiotherapy. A retrospective review of 107 patients." *Aust N Z J Surg* 9, 670-674; Osteen, R. T., Karnell, L. H. (1994) "The national cancer data-base report on breast-cancer." *Cancer* 73, 1994-2000). Notably, modified radical mastectomies lead to seroma formation rates ranging from 15 to 38.6%, while radical mastectomies report a rate as high as 52% (Budd, supra; Hayes, J. A., Bryan, R. M. (1984) "Wound-healing following mastectomy." *Aust N Z J Surg* 54, 25-27; Aitken, D. R., Hunsaker, R., James, A. G. (1984) "Prevention of seromas following mastectomy and axillary dissection." *Surg Gynecol Obstet* 158, 327-330; Chilson, T. R., Chan, F. D., Lonser, R. R., Wu, T. M., Aitken, D. R. (1992) "Seroma prevention after modified radical-mastectomy." *Am Surg* 58, 750-754; Terrell, G. S., Singer, J. A. (1992) "Axillary versus combined axillary and pectoral drainage after modified radical-mastectomy." *Surg Gynecol Obstet* 175, 437-440).

As an example, in the course of performing a radical mastectomy, the surgeon removes substantially all of the patient's breast tissue between the rib cage and a relatively large area of overlying skin. Following surgery, it is necessary for the resulting relatively large flap of skin to heal with and adhere to the underlying tissue. However, an accumulation of serous fluid tends to collect between the overlying skin flap and the underlying tissue. This collection of serious fluid tends to prevent the skin from healing with the subcutaneous tissue and deep fascia, and also provides a medium highly susceptible to infection.

In current clinical practice, silicone surgical drains are placed in the wound bed through separate stab incisions to collect transudate fluid but they can be a significant source of pain and discomfort to patients, especially upon their removal up to several weeks after the initial surgical procedure. Furthermore, these procedures can further increase the risk of infection at the surgical site.

Provided pDHA copolymers can be used to treat and prevent seromas resulting from a variety of surgical procedures. Such procedures include, without limitation, cancer resection and general surgery procedures such as mastectomies, lumpectomies, embolectomies; lipoma excisions, hysterectomies, plastic surgery procedures such as abdominoplasties, forehead lifts, buttocks lifts, face lifts, liposuction, skin grafts, implant surgery (e.g., calf, bicep, tricep, pectoral, penile, subdermal, transdermal, dental, bone), rhytidectomies or rhinoplasties; mammaplasties; biopsy closure, cleft-palate reconstruction, incidional hernia repair, lymph node resection, groin repair, Caesarean section, laparoscopic trocar repair, vaginal tear repair, orthopedic procedures, laminectomies, treatment of traumatic lesions, fistula treatment, graft fixation, nerve repair, electrocautery procedures, resection of the thyroid or parathyroid glands, dental procedures such as tooth extraction, and hand surgery. Provided pDHA copolymers are also useful in the treatment and prevention of seromas that may result from veterinary surgical procedures.

Tissue Adhesion

Provided pDHA copolymers are useful in the prevention of postoperative tissue adhesion. Adhesions which may be formed include the adhesion of tissue to tissue or of tissue to bone. As generally known, the occurrence of post-operative adhesion formation after internal surgery is a major problem in abdominal surgery. For example, tissue adhesion complications may affect fertility in gynecological patients. Because adhesions occur in about 70% of the gynecological abdominal surgical interventions, it is evident that there is a need for a suitable method for preventing the above-identified adhesions, and the complications and patient discomfort associated therewith.

It has been known to separate adjacent internal bodily surfaces by interposing a mesh or film so that during tissue regeneration following surgery no contact exists between the surfaces. One material which has been employed to prevent adhesions is an expanded polytetrafluoroethylene material known as Gore-Tex®. This material, however, is not hemostatic and is non-degradable by the human body. Thus the implant remains in the body, and, if necessary, must be removed surgically following the healing process. Another material is a mesh barrier of carboxymethylcellulose known as Interceed®. This material, however, may not be applied in a blood-rich environment as under such circumstances the material quickly loses its barrier function. Others have disclosed firms of poly(ethyleneoxide) and polyethylene terephthalate as barrier materials to prevent surgical adhesions (Gilding and Reed, in *Polymer*, Vol. 20 pgs. 1454-1458 (December 1979) and in *Polymer*, Vol. 22, pgs. 499-504 (April 1981).

The present disclosure provides a method for the prevention or treatment of post-operative tissue adhesion, the method comprising the step of: administering a material comprising a poly-dihydroxyacetone copolymer at or near a wound bed or surgical site. The present disclosure also provides a method for achieving hemostasis, the method comprising the step of: administering a material comprising a poly-dihydroxyacetone (pDHA) copolymer at or near a wound bed or surgical site.

Hemostasis

The present disclosure provides a method for achieving hemostasis, the method comprising the step of: administering a material comprising a poly-dihydroxyacetone (pDHA) copolymer at or near a wound bed or surgical site. In certain embodiments, the wound bed or surgical site comprises a hepatic surface. In certain embodiments, the step of administering a material comprising a poly-dihydroxyacetone (pDHA) copolymer comprises dusting the material onto the bleeding surface.

In certain embodiments, the methods described herein are palliative with respect to the conditions being treated. In certain embodiments, the methods are preventative. In certain embodiments, the methods are curative.

The present disclosure provides "pharmaceutically acceptable" compositions, which comprise a therapeutically effective amount of one or more of the compounds described herein, formulated together with one or more pharmaceutically acceptable carriers (additives) and/or diluents. As described in detail, the pharmaceutical compositions of the present disclosure may be specially formulated for administration in solid or liquid form, including those adapted for the following: parenteral administration, for example, by subcutaneous, intramuscular, intravenous or epidural injection as, for example, a sterile solution or suspension; topical application, for example, as a cream, ointment, or a controlled-release patch.

The present disclosure further provides kits comprising compositions of pDHA copolymers. The kit optionally includes instructions for preparing and/or administering a provided composition. In certain embodiments, the kit includes multiple doses of the composition. In certain embodiments, the kit includes additional components or tools useful for the preparation and/or administration of a composition. The kit may include sufficient quantities of each component to treat a subject for a week, two weeks, three weeks, four weeks, or multiple months.

EXAMPLES

In addition to those described herein, methods of preparing poly-dihydroxyacetone and derivatives thereof are described in U.S. Patent Publication No. 2008/0194786, the entire contents of which are hereby incorporated by reference.

General Procedures

Monomethoxy-poly(ethylene glycol) (MPEG) ($M_w$ 5000) was purchased from Polysciences (Warrington, Pa.). Prior to use, MPEG was dried by azeotropic distillation in toluene. Dihydroxyacetone dimer (DHA), p-toluene sulfonic acid, trimethyl orthoformate, $Sn(Oct)_2$, ethyl chloroformate, and 5% phosphotungstic acid were purchased from Sigma-Aldrich (St. Louis, Mo.) and used as received. Triethylamine, tetrahydrofuran (THF), dichloromethane ($CH_2Cl_2$), diethyl ether, methanol, toluene, and TFA were purchased from VWR (West Chester, Pa.) and used as received. Syringes and PBS (pH 7.4) were purchased from Fisher Scientific. Collagen was purchased from MP Biomedicals.

$^1$H NMR spectra were recorded on a Mercury 300 spectrometer. Gel permeation chromatography (GPC) was carried out using PSS SDV columns 500A, 50A, and linear M (in series) with a THF mobile phase (1 ml/min) and polystyrene standards with UV (Waters 486) and RI (Waters 2410) detection. Rheology measurements were performed using a Physica Modular Compact 300 Rheometer. Scanning Electron Microscopy (SEM) measurements were performed using the LEICA 440.

The swelling degree (S.D.) of provided polymers was obtained by hydrating 30 mg of each MPEG-pDHA molecular weight (n=4) in 1.0 mL of PBS at room temperature. The gels were allowed to sit for approximately 4 minutes on a filter paper to drain the excess PBS. The gels were weighed to obtain the swollen weight ($W_s$), then lyophilized and weighed again to obtain the dry weight ($W_d$). S.D. was calculated using equation 1 (Barbucci, R., Rappuoli, R., Borzacchiello, A., Ambrosio, L. (2000) "Synthesis, chemical and rheological characterization of new hyaluronic acid-based hydrogels." *J Biomat Sci-Polym E* 11, 383-399):

$$S.D. (\%) = (W_s/W_d) * 100 \qquad (1)$$

Rheological tests were performed using a Physica Modular Compact 300 using parallel plate geometry (8 mm diameter parallel plate). Data was recorded using US200 software and analyzed using an Excel spreadsheet. All experiments were performed at 28 and 37° C. The viscoelastic properties of the gels were determined by performing frequency sweep experiments in the oscillatory mode with a 1% strain amplitude and frequency range of 0.1-100 l/s. Step stain experiments, with a 1% strain, were performed to determine the stress relaxation of the gels.

Entanglement density was calculated using the plateau storage modulus, $G_e$ (the maximum G' where G'/G">1) (Rubinstein, M., Colby, R. (2003) *Polymer Physics* (Oxford University Press, NYC); Macosko, C. W. (1994) *Rheology: Principles, Measurements, and Applications* (VCH Publishers, NYC). Using Equation 2:

$$G_e = \nu kT \quad (2)$$

wherein:

$G_e$ is the plateau G', $\nu$ is the entanglement density (m$^{-3}$), k is the Boltzman constant (kg·m$^2$·s$^{-2}$·K$^-$), and T is the temperature (K).

Figure 10:
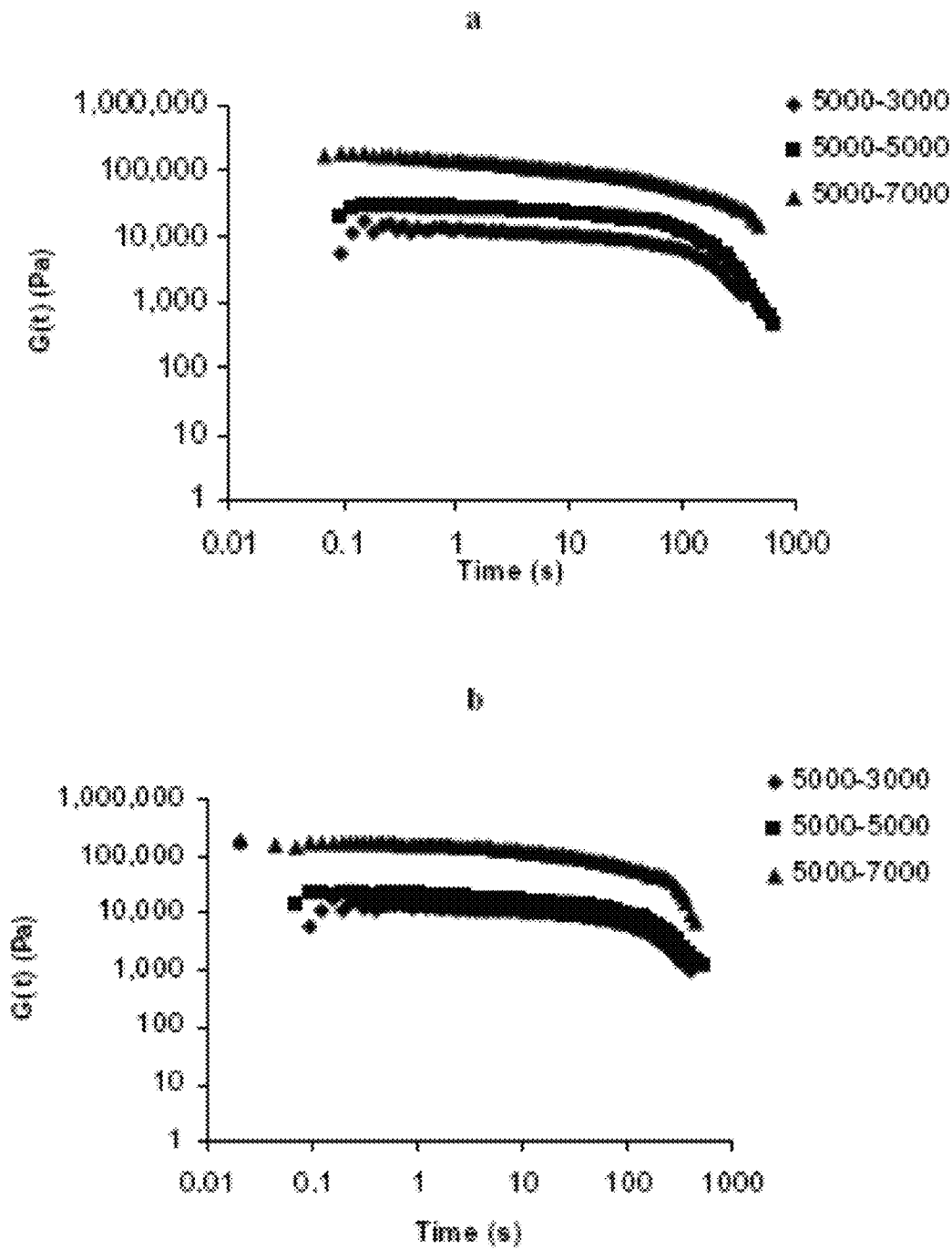
FIG. 10 depicts relaxation modulus G(t) results on a MPEG-pDHA gel at a 1% strain. (a) 28° C., (b) 37° C. These results are used to calculate the gel relaxation kinetics.

Calculation of the chain relaxation time ($\tau$) was obtained my measuring the relaxation modulus (G(t)) following a small step strain (as shown in FIG. 10). Using equation 3 (Rubinstein and Macosko, supra).

$$G(t) = G(\tau)\exp^{-t/\tau} \quad (3)$$

wherein:

G(t) is the relaxation modulus (Pa),

G($\tau$) is constant (Pa), t is time (s), and $\tau$ is the chain relaxation time (s).

Differentiating and rearranging equation (3) yields:

$$[tG(t)]' = G\exp^{-\left(\frac{t}{\tau}\right)}\left(1 - \frac{t}{\tau}\right) \quad (4)$$

Using equation 4, a plot of tG(t) vs. t yields a plot with a maximum at t=$\tau$, which is the chain relaxation time ($\tau$).

Example 1

Polymer Synthesis

Figure 6:
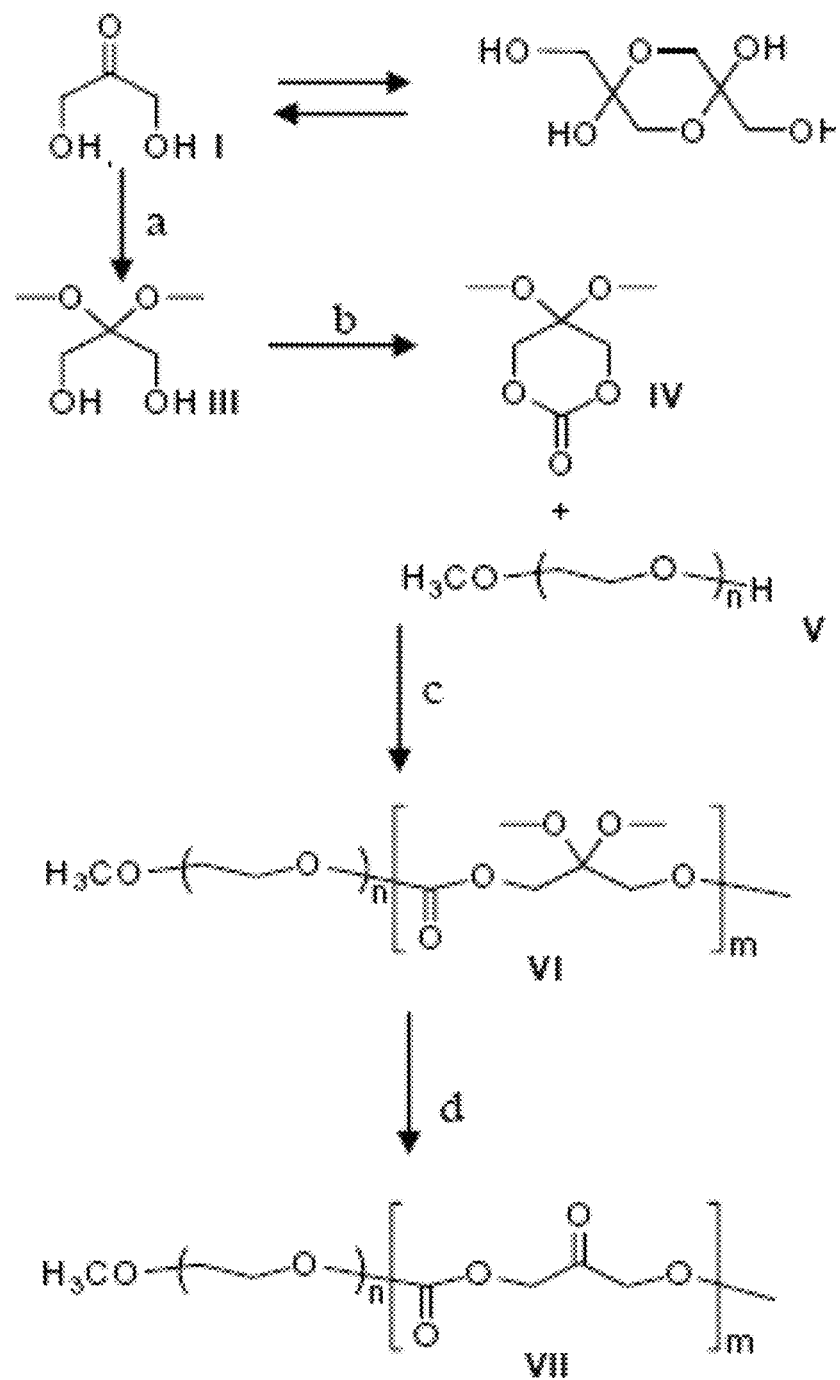
FIG. 6 depicts a synthetic route to poly(MPEG-b-2-oxypropylene carbonate), MPEG-pDHA (VII). (a) Trimethyl orthoformate/p-toluene sulfonic acid, (b) ethylchloroformate/triethylamine, (c) stannous octoate/100° C., (d) trifluoroacetic acid/$H_2O$. Nomenclature: (I) DHA; (II) DHA dimer; (III) 2,2-dimethoxy-1,3-propane diol; (IV) 2,2-dimethoxy-1,3-propylene carbonate; (V) Monomethoxy-PEG (MPEG); (VI) poly(MPEG-b-2,2-dimethoxy-1,3-propylene carbonate); (VII) poly(MPEG-b-2-oxypropylene carbonate) (pDHA) (Zawaneh, infra). Reproduced with permission from *Biomacromolecules* 2006, 7, 3245-3251. Copyright 2006 American Chemical Society.

Poly(MPEG-b-2-oxypropylene carbonate) (VII) (MPEG-pDHA) was synthesized using a previously published protocol (Zawaneh, supra). Briefly, dihydroxyacetone dimer (II) was locked in its monomeric form by conversion of its C2 carbonyl group into a dimethoxy acetal using trimethyl-orthoformate and p-toluenesulfonic acid (III) (See FIG. 6). This was then converted to a 6-membered cyclic carbonate (IV). IV was polymerized using Sn(Oct)$_2$ in the presence of monomethoxy poly(ethylene glycol) (MPEG) to form (VI). The molecular weight of the MPEG was fixed at 5000, while the molecular weight of the DHA based polymer chain was varied depending on the reactant feed ratios and the Sn(Oct)$_2$ injection conditions (molecular weights of 3000, 5000, 7000, and 10000 were synthesized). This polymer was subsequently deprotected using a TFA-water mixture (4:1) to produce the desired polymer, MPEG-pDHA (VII). The amount of TFA-water needed to deprotect the polymer depended on the length of the pDHA based segment. Table 1 summarizes the polymerization conditions used to synthesize each molecular weight. The reaction scheme is also shown in FIG. 6. MPEG-pDHA $^1$H NMR (DMSO-d$_6$) δ: 5.00 (s; 4H), 3.50 (s; 4H), 3.24 (s; 3H).

TABLE 1

Summary of the polymerization and deprotection conditions used.

| MPEG-pDHA | MPEG feed (mg) | IV feed (mg) | Sn(Oct)$_2$ (μL) | Sn(Oct)$_2$ injection temp (° C.) | TFA-H$_2$O: VI (mL/100 mg) |
|---|---|---|---|---|---|
| 5000-3000 | 550 | 470 | 10 | 25 | 0.92 |
| 5000-5000 | 250 | 420 | 10 | 100 | 1.30 |
| 5000-7000 | 150 | 420 | 8 | 100 | 1.50 |
| 5000-10000 | 100 | 520 | 8 | 100 | 1.80 |

TABLE 2

Summary of selected MPEG-pDHA gel swelling measurements, cross link density, and chain relaxation times following shear. Increasing the pDHA chain length reduces the extent of swelling and increases the hydrogel cross link density and relaxation time.

| Sample MPEG-pDHA | Weight gain swelling (%) | Entanglement density $\nu$ (m$^{-3}$) | Relaxation time $\tau$ (s) |
|---|---|---|---|
| 5000-3000 | 587.5 ± 18.3 | 4.96e24 | 250 |
| 5000-5000 | 513.1 ± 12.2 | 1.48e25 | 250 |
| 5000-7000 | 396.0 ± 22.3 | 3.25e25 | 350 |

Hydrogel Characterization

Figure 2:
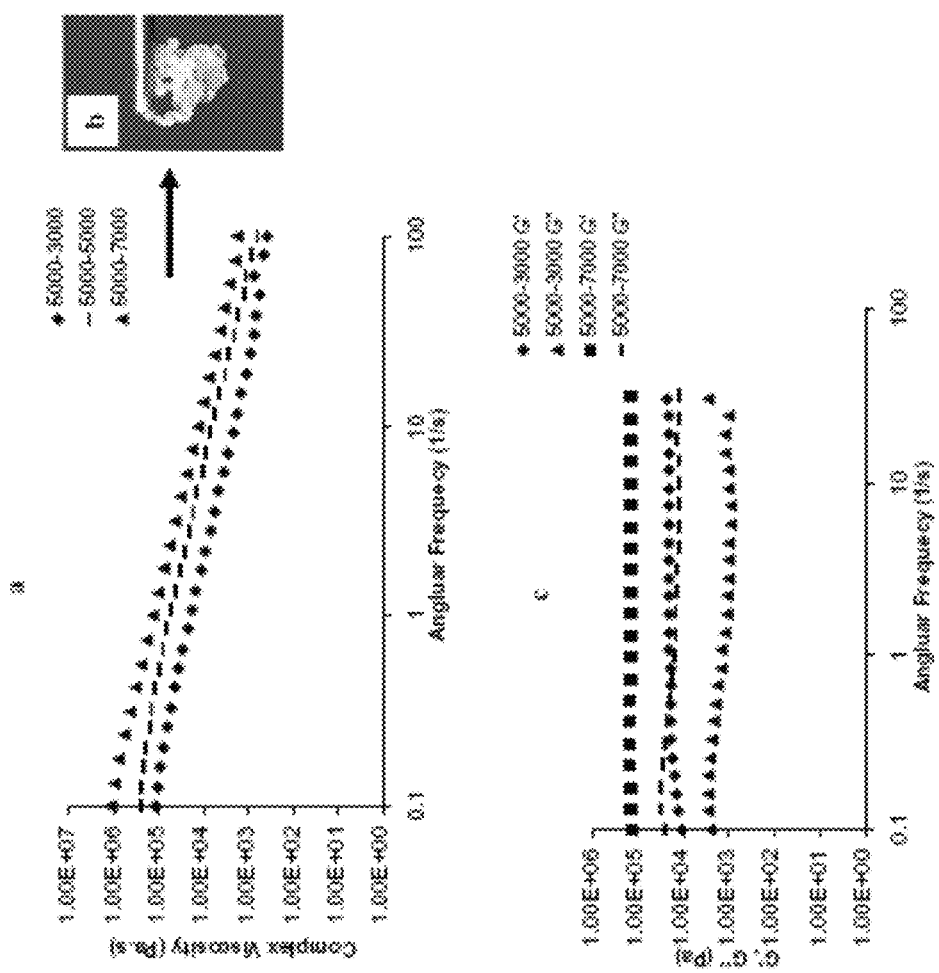
FIG. 2 depicts characterization data for MPEG-pDHA. (a) Viscosity readings demonstrate the MPEG-pDHA hydrogel thixotropic behavior (1% strain, 28° C.). (b) An example of MPEG-pDHA 5000-5000 extruded from a 26 G needle. (c) G' and G" readings as obtained from frequency sweep experiments on the MPEG-pDHA gels (1% strain, 28° C.).
Figure 7:
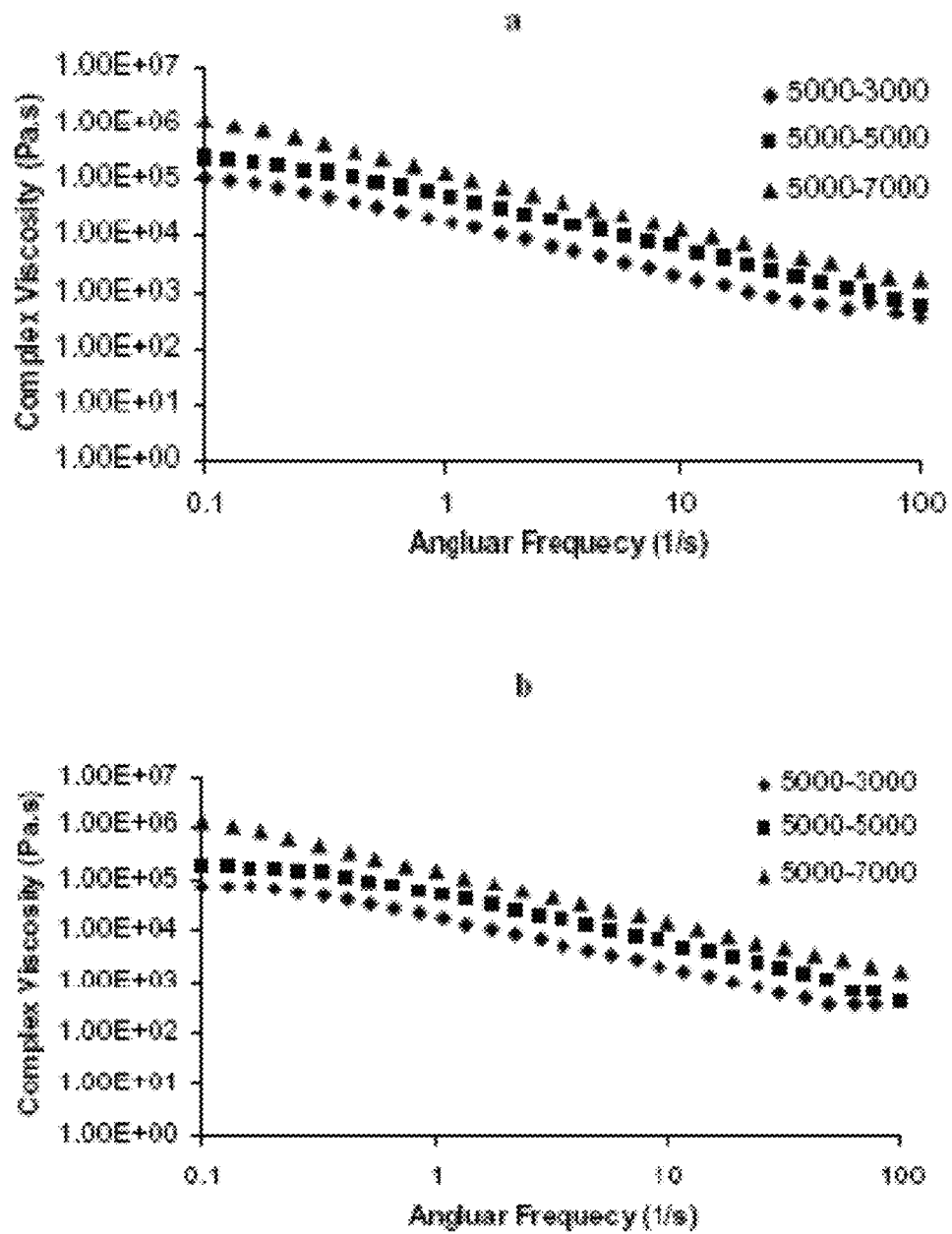
FIG. 7 depicts a frequency sweep experiment on a MPEG-pDHA hydrogel at a 1% strain (a) 28° C., (b) 37° C. The materials display a trend of decreasing viscosities with increasing shear rates (thixotropic behavior). Increasing the temperature has no effect on the hydrogel viscosity.

In some embodiments, MPEG-pDHA hydrogels are thixotropic and exhibit a trend of decreasing viscosities with increasing shear rates (FIG. 2a). This thixotropic nature allows hydrogels to form extrudable materials that can be delivered (e.g., to a seroma) by injection even at remote sites. An increase in pDHA chain length and subsequent increase in entanglement density lead to an increase in hydrogel viscosity (FIG. 2a). FIG. 2b illustrates an example of MPEG-pDHA 5000-5000 upon extrusion from a narrow-bore 26 G hypodermic needle. A complete set of viscosity measurements at 28° C. and 37° C. is provided in FIG. 7.

Figure 8:
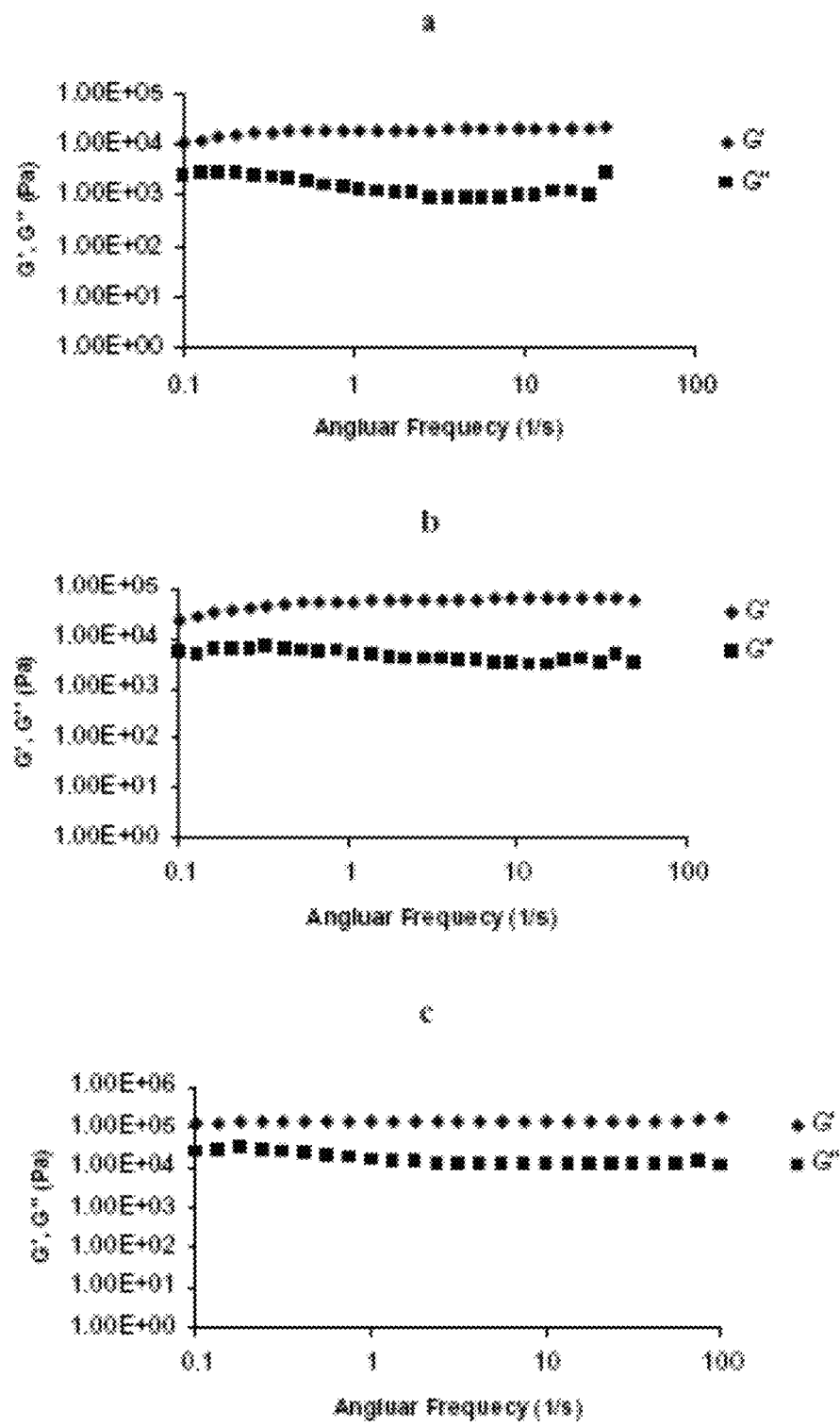
FIG. 8 depicts a frequency sweep experiment on a MPEG-pDHA hydrogel at 28° C. and a 1% strain. (a) 5000-3000, (b) 5000-5000, (c) 5000-7000. G' values are greater than G" values across the entire frequency range, a characteristic typical of elastic hydrogels. G' and G" values are used to calculate gel entanglement density.
Figure 9:
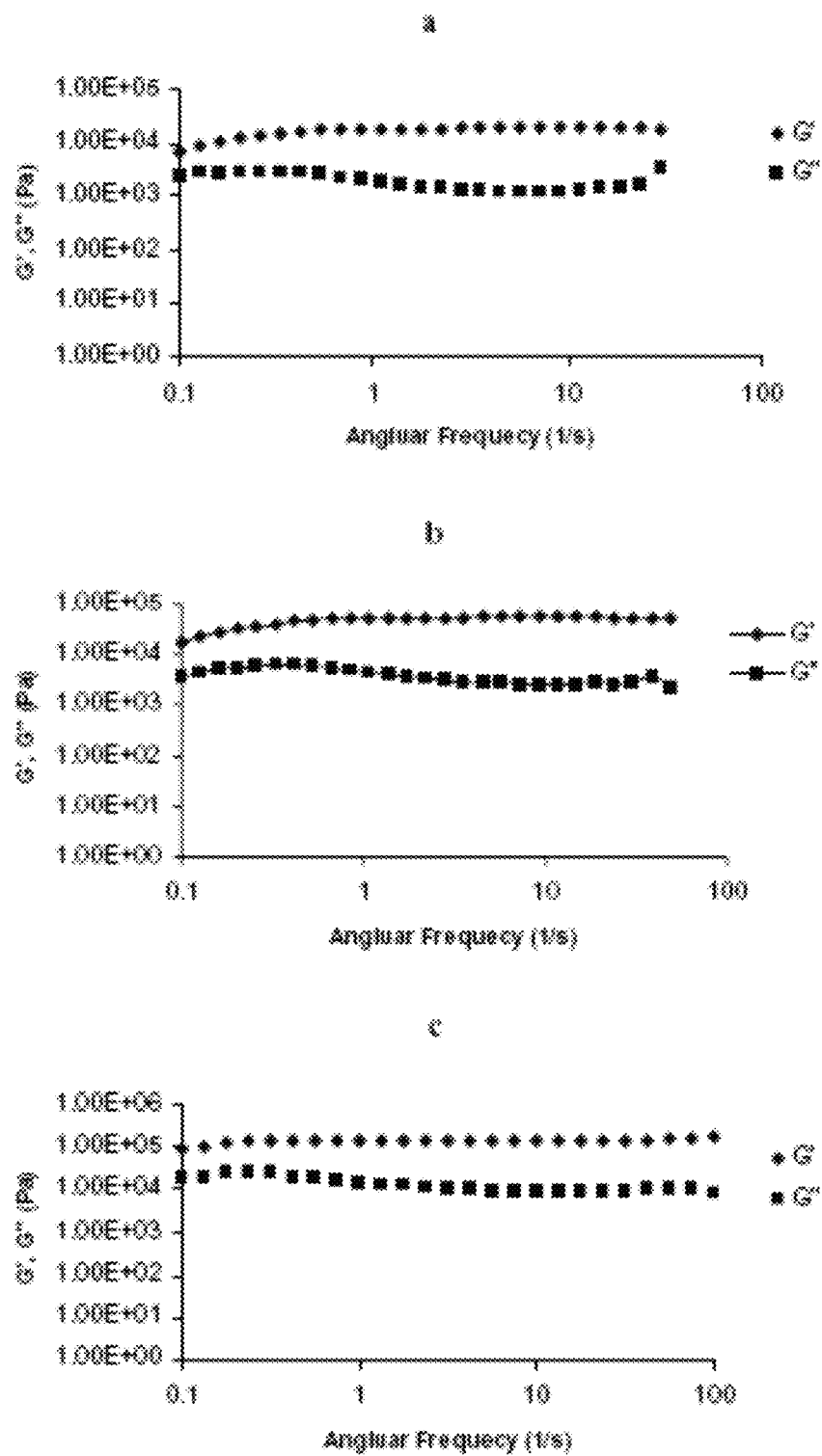
FIG. 9 depicts a frequency sweep experiment on a MPEG-pDHA gel at 37° C. and a 1% strain. (a) 5000-3000, (b) 5000-5000, (c) 5000-7000. G' values are greater than G" values across the entire frequency range, a characteristic typical of elastic hydrogels. G' and G" values are used to calculate gel entanglement density.

In certain embodiments, controlling a hydrogel's entanglement density is useful for controlling its viscosity and porosity. Entanglement densities are calculated from the storage (G') and loss (G") moduli measurements (as detailed above), which also provide insight into the elastic nature of the gels. FIG. 2c is an example of a typical G' and G" graph as obtained for an MPEG-pDHA hydrogel (5000-3000 and 5000-7000). The G' values display very low frequency dependence and are greater than G" values across the entire frequency range, a trend characteristic of elastic hydrogels (Vermonden, T., Besseling, N. A. M., van Steenbergen, M. J., Hennink, W. E. (2006) "Rheological studies of thermosensitive triblock copolymer hydrogels." *Langmuir* 22, 10180-10184; Nowak, A. P., et al. (2002) "Rapidly recovering hydrogel scaffolds from self-assembling diblock copolypeptide amphiphiles." *Nature* 417, 424-428). The G' and G" values also increase with increasing pDHA chain length and entanglement density. A complete set of G' and G" measurements is provided in FIGS. 8 and 9.

MPEG-pDHA chain relaxation time was calculated from the rheological data. Relaxation calculations help determine the hydrogel relaxation kinetics following a step strain, which can provide insight into how long it takes the MPEG-pDHA hydrogel chains to relax to their equilibrium state following injection at the seroma site. Rapid relaxation times help ensure that a biomaterial rapidly reverts to its equilibrium state, and subsequently reduce the number of variables that can influence the performance of a therapeutic hydrogel in vivo. In some embodiments, MPEG-pDHA gels display rapid relaxation times (250-350 s) which also increase with increasing pDHA chain length and entanglement density (See Table 2) (Sahiner, N., Singh, M., De Kee, D., John, V. T., McPherson, G. L. (2006) "Rheological characterization of a charged cationic hydrogel network across the gelation boundary." Polymer 47, 1124-1131). Equations that were used to calculate MPEG-pDHA hydrogel relaxation times are shown above. A complete set of chain relaxation data is provided in FIG. 10 and Table 3.

TABLE 3

Relaxation times of MPEG-pDHA. The relaxation times increase with increasing pDHA chain length.

| MPEG-pDHA | $\tau$ (s) at 28° C. | $\tau$ (s) at 37° C. |
|---|---|---|
| 5000-3000 | 250 | 250 |
| 5000-5000 | 250 | 250 |
| 5000-7000 | 350 | 300 |

Example 2

In Vitro Hydrolytic Degradation

In vitro degradation studies were performed on MPEG-pDHA 5000-3000, 5000-5000, and 5000-7000. The polymer samples were weighed out into 20 mg samples and placed in 1.0 mL PBS (pH=7.4) 1.5 mL Eppendorf tubes. The samples were placed on an orbital shaker and incubated at 37° C. Samples were recovered for each polymer at the selected time points (n=3). The samples were recovered, washed with DI water, lyophilized, and re-weighed. Degradation products from fully degraded samples were characterized by $^1$H NMR. $^1$H NMR ($D_2O$) DHA $\delta$: 4.40 (s; 4H), 3.55 (s; 6H). $^1$H MPEG ($D_2O$) DHA $\delta$: 3.70 (s; 4H).

Example 3

Anti-Seroma Efficacy (In Vivo)

Figure 4:
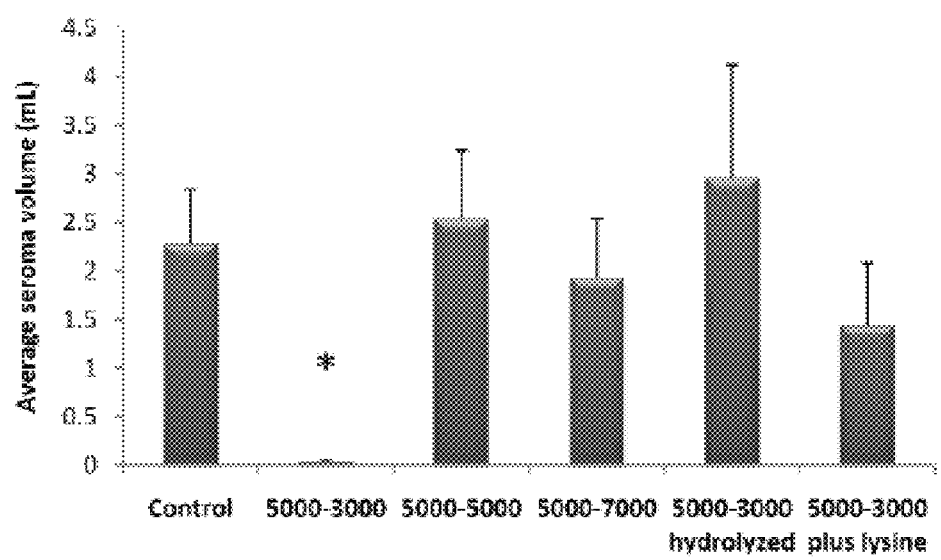
FIG. 4 depicts seroma volumes from a rat mastectomy model. The untreated controls displayed a mean seroma volume of 2.28±0.55 mL (n=6). MPEG-pDHA 5000-3000 treated rats displayed a mean seroma volume of 0.044±0.017 mL (n=9, p<0.01). MPEG-pDHA 5000-5000 treated rats displayed a mean seroma volume of 2.53±0.70 (n=8). MPEG-pDHA 5000-7000 treated rats had a mean seroma volume of 1.93±0.60 (n=8). Treatment with both hydrolyzed and lysine-treated MPEG-pDHA did not result in statistically significant reduction in seroma volume relative to untreated control (2.6±1.16, n=6, and 1.41±0.63, n=6, respectively)
Figure 12:
FIG. 12 depicts a photograph of surgical cavity showing residual MPEG-pDHA 24 hours post surgery.
Figure 13:
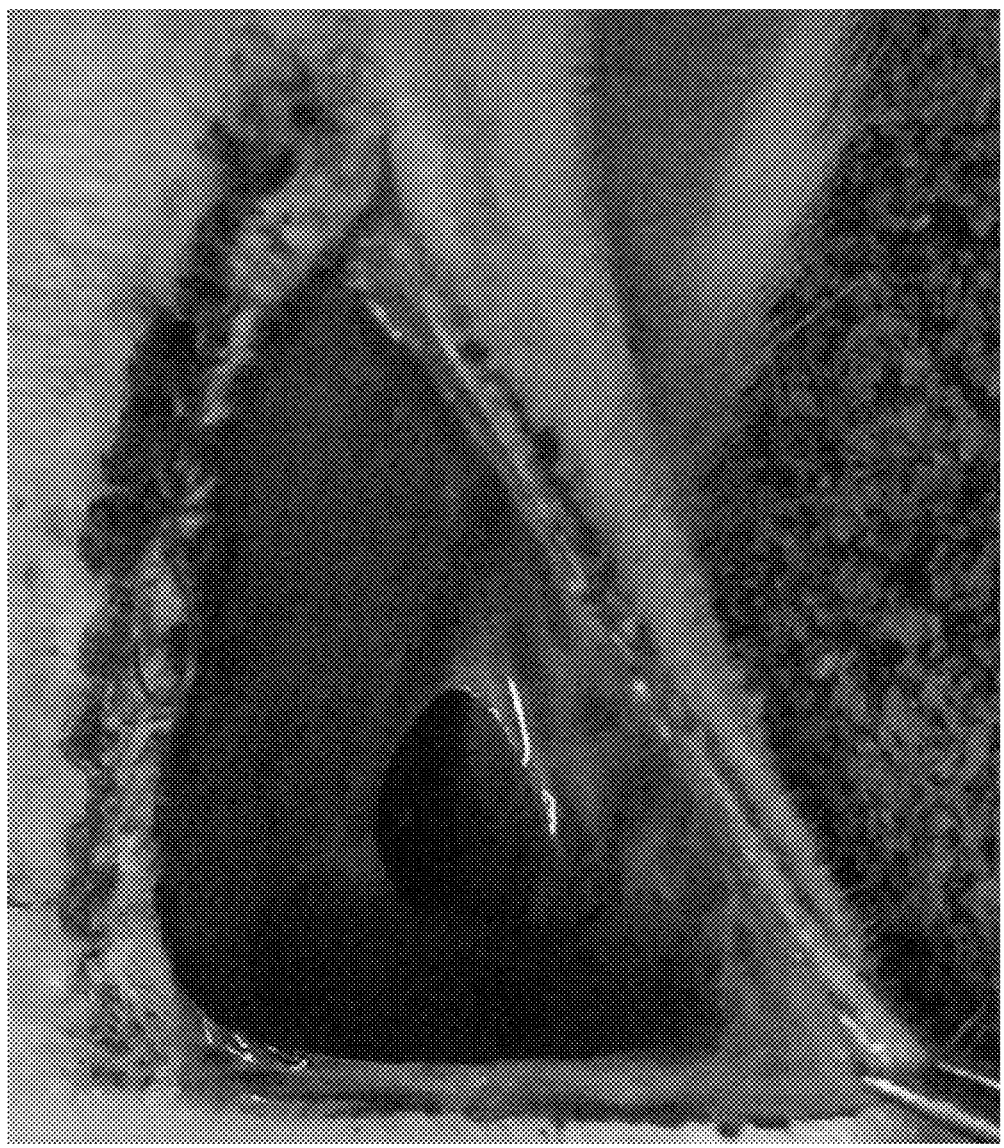
FIG. 13 depicts a photograph of surgical cavity showing the absence of MPEG-pDHA 72 hours post surgery.

Following the rheological and degradation characterization of MPEG-pDHA, we evaluated how hydrogels performed in a potential surgical application, the prevention of postoperative seroma. A well-established rat mastectomy model was used to determine the efficacy of MPEG-pDHA, and to allow direct comparison to the literature (Silverman, supra). As shown in FIG. 4, the untreated controls displayed a mean seroma volume of 2.28±0.55 mL, whereas MPEG-pDHA 5000-3000 treated rats displayed a significantly decreased mean seroma volume of 0.044±0.017 mL (p<0.01). Interestingly, MPEG-pDHA 5000-5000 and 5000-7000 treated rats displayed a mean seroma volume of 2.53±0.70 (p=0.8) and 1.93±0.60 (p=0.2), respectively which are statistically equivalent to the untreated control animals. Post-mortem examination of animals treated with MPEG-pDHA 5000-3000 demonstrated gross fibrinous adhesions between the elevated skin flap and chest wall whereas no adhesions were evident in the other treatment or control groups. In vivo degradation of the polymer was confirmed by the absence of residual polymer (all three compositions) upon histological examination of excised tissue from the wound bed at seven days after application. At day 1 post surgery residual MPEG-pDHA was evident (FIG. 12), suggesting the in vivo rate of degradation is slower than observed in vitro, however, no residual polymer was visualized on day 3 (FIG. 13).

Figure 5:
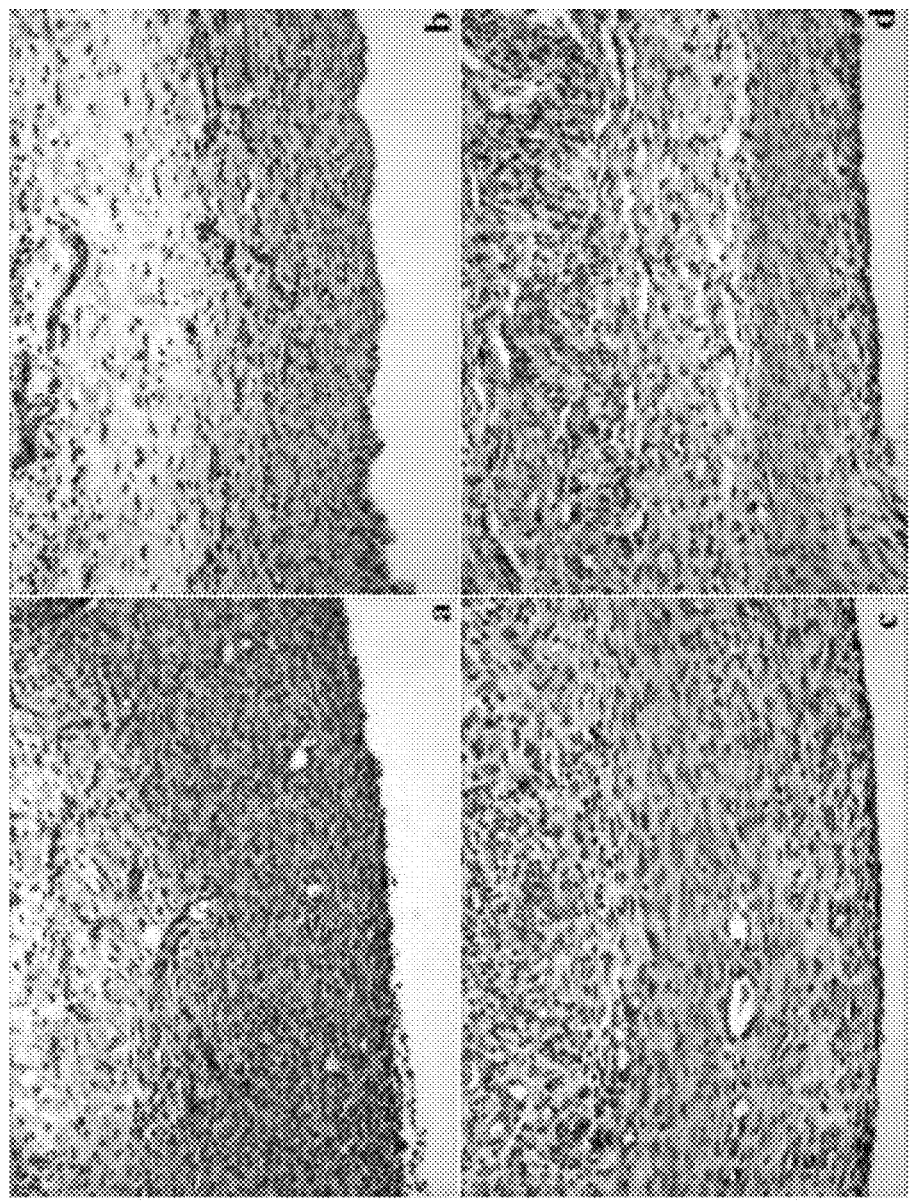
FIG. 5 depicts light microscopic appearance of surgical sites at 7 days (a) control, (b) MPEG-pDHA 5000-3000, (c) MPEG-pDHA 5000-5000, and (d) MPEG-pDHA 5000-7000. The sections show early granulation tissue adjacent to surgical site, which is the clear space at the bottom of all images. H&E stain, 100× magnification.

With respect to biocompatibility, there was normal-appearing early granulation tissue and a mild inflammatory response that was equal to untreated control animals (FIG. 5). These results suggest that MPEG-pDHA and its degradation products are well tolerated by the soft tissue surrounding the wound bed and do not negatively impact the normal sequence of early wound healing.

Experimental

To evaluate the efficacy of the polymer gels, each MPEG-pDHA based gel was evaluated in a well established rat model of seroma formation (Lindsey, supra). Briefly, following a midline incision, a skin flap was raised over the right chest, exposing the right pectorals major muscle which was then excised. A right axillary lymphadenctomy was then performed under an operating microscope. The fully hydrated hydrogel was prepared freshly to full hydration by mixing 100 mg of lyophilized MPEG-pDHA powder with sterile saline over filter paper. Experimental rats received 0.5 cc of MPEG-pDHA hydrogel into the wound bed before closure while controls received 0.5 cc of saline into the wound bed before closure.

Animals were sacrificed on post operative day seven by carbon dioxide asphyxiation followed by cervical dislocation as per institutional guidelines approved for such investigation. Seroma fluid was aspirated percutaneously via an 18 gauge needle and measured volumetrically. The incision site was then opened and any remaining seroma fluid was removed by needle aspiration. To determine in vivo biocompatibility of the polymer, sections of the skin flap and the underlying wound bed were removed en bloc and analyzed histologically (H+E stain) for evidence of residual polymer and inflammation in the area of application. A student two tail t-test with unequal variance was performed to determine the p value ($\alpha$=0.05).

Example 4

To make a correlation between anti-seroma efficacy and the polymer structure, we conducted three mechanism-oriented experiments. First, we degraded MPEG-pDHA 5000-3000 in water into oligomeric products to ascertain whether the polymer degradation products were a causative factor in seroma prevention. As shown in FIG. 4, hydrolyzed MPEG-pDHA was ineffective, suggesting the full length polymer upon administration is necessary for anti-seroma activity. Second, the MPEG-pDHA hydrogel was hydrated in the presence of a 2-fold mole excess of lysine (relative to C2 carbonyl groups) to determine whether the C2 carbonyl reactivity with the primary amines in the tissue was necessary for anti-seroma activity. The lysine was added to occupy the C2 carbonyl groups, therefore, if C2 reactivity with the amines in the tissue is necessary for activity, the lysine-hydrated formulation should be less active. As shown in FIG. 4, although the lysine-hydrated formulation showed a reduced seroma volume, the reduction was statistically equivalent to the control, suggesting that the reactivity of the C2 carbonyl takes part in preventing seroma. Third, to determine if MPEG-pDHA initiated the clotting cascade to facilitate tissue integration, we measured the effect of the polymer on prothrombin time (PT) and partial thromboplastin time (PTT). The results show that the biomaterial has no effect on PT and PTT suggesting that activation of the clotting cascade is not a factor in seroma prevention. Additional details, including experiments describing the hemostatic efficacy of provided copolymers, are described by Henderson, P. W., et al. (2009) "A rapidly resorbable hemostatic biomaterial based on dihydroxyacetone." *Journal of Biomedical Materials Research Part A*. DOI: 10.1002/jbm.a.32586), the entire contents of which is incorporated by reference.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

What is claimed is:

1. A hydrogel having a physically entangled network of poly(ethylene glycol)/poly-dihydroxyacetone (PEG-pDHA) copolymer, wherein the (PEG-pDHA) copolymer is a block copolymer comprising a PEG block, wherein the PEG block is branched.

2. The hydrogel of claim 1, wherein the (PEG-pDHA) copolymer is thixotropic.

3. A copolymer comprising DHA and glycerol.

4. The copolymer of claim 3, comprising a first block of PEG; and a second block of polymer comprising DHA and glycerol.

5. The copolymer of claim 3, comprising DHA, glycerol, and PEG.

6. A hydrogel having a physically entangled network of poly(ethylene glycol)/poly-dihydroxyacetone (PEG-pDHA) copolymer, wherein the (PEG-pDHA) copolymer is a random copolymer.

7. The hydrogel of claim 1, wherein the (PEG-pDHA) copolymer is a PEG-pDHA diblock copolymer comprising a PEG block and a pDHA block.

8. The hydrogel of claim 7, wherein the $M_w$ of the PEG block of the PEG-pDHA diblock copolymer is from 100 to 1,000,000 daltons.

9. The hydrogel of claim 8, wherein the $M_w$ of the PEG block of the PEG-pDHA diblock copolymer is from 100 to 10,000 daltons.

10. The hydrogel of claim 7, wherein the $M_w$ of the pDHA block of the PEG-pDHA diblock copolymer is from 100 to 1,000,000 daltons.

11. The hydrogel of claim 10, wherein the $M_w$ of the pDHA block of the PEG-pDHA diblock copolymer is from 1,000 to 10,000 daltons.

12. The hydrogel of claim 11, wherein the $M_w$ of the pDHA block of the PEG-pDHA diblock copolymer is from 2,500 to 3,500 daltons.

13. The hydrogel of claim 1, wherein the branched PEG block comprises 3 to 50 PEG chains emanating from a central core group.

14. The hydrogel of claim 1, wherein the PEG block is a comb PEG.

15. The hydrogel of claim 1, wherein the PEG block is a star PEG.

16. The hydrogel of claim 15, wherein the star PEG comprises 3 to 200 PEG chains emanating from a central core group.

17. A hydrogel having a physically entangled network of poly(ethylene glycol)/poly-dihydroxyacetone (PEG-pDHA) copolymer, wherein the (PEG-pDHA) copolymer is a PEG-pDHA diblock copolymer comprising a PEG block, wherein the PEG block is terminated with an organic group selected from the group consisting of carbohydrates, proteins, and peptides.

18. The copolymer of claim 3, wherein the copolymer is a block copolymer.

19. The copolymer of claim 3, wherein the copolymer is a random copolymer.

20. The copolymer of claim 4, wherein the second block is a block copolymer.

21. The copolymer of claim 4, wherein the second block is a random copolymer.

* * * * *